(12) United States Patent
McFadden et al.

(10) Patent No.: US 7,718,368 B2
(45) Date of Patent: May 18, 2010

(54) IMMUNOMODULATORY PROTEIN AND USEFUL EMBODIMENTS THEREOF

(75) Inventors: Grant McFadden, London (CA); Alexandra Lucas, London (CA); Xing Li, London (CA)

(73) Assignee: Viron Therapeutics Inc., London (CA)

( * ) Notice: Subject to any disclaimer, the term of this patent is extended or adjusted under 35 U.S.C. 154(b) by 142 days.

(21) Appl. No.: 11/505,682

(22) Filed: Aug. 17, 2006

(65) Prior Publication Data

US 2009/0011979 A1 Jan. 8, 2009

Related U.S. Application Data

(63) Continuation-in-part of application No. 10/455,000, filed on Jun. 4, 2003, now Pat. No. 7,101,559, which is a continuation-in-part of application No. PCT/CA01/01734, filed on Dec. 4, 2001.

(60) Provisional application No. 60/251,147, filed on Dec. 4, 2000.

(51) Int. Cl.
C12Q 1/68 (2006.01)
(52) U.S. Cl. ........................ 435/6; 424/204.1
(58) Field of Classification Search .............. 424/204.1; 435/6; 530/300
See application file for complete search history.

(56) References Cited

U.S. PATENT DOCUMENTS

| | | | |
|---|---|---|---|
| 5,651,972 A | 7/1997 | Moyer et al. | |
| 5,656,465 A | 8/1997 | Panicali et al. | |
| 5,686,409 A | 11/1997 | McFadden et al. | |
| 5,834,419 A | 11/1998 | McFadden et al. | |
| 5,871,740 A | 2/1999 | Smith | |
| 5,939,525 A | 8/1999 | McFadden et al. | |
| 6,495,515 B1 | 12/2002 | McFadden et al. | |
| 6,559,298 B1 | 5/2003 | Torigoe et al. | |
| 6,562,376 B2 | 5/2003 | Hooper et al. | |
| 6,589,764 B1 | 7/2003 | Sims et al. | |
| 6,589,933 B1 | 7/2003 | McFadden et al. | |
| 6,605,280 B1 | 8/2003 | Novick et al. | |
| 6,894,155 B2 | 5/2005 | McFadden et al. | |
| 7,101,559 B2 | 9/2006 | McFadden et al. | |
| 2002/0102535 A1* | 8/2002 | McFadden et al. | ............. 435/5 |
| 2004/0038203 A1 | 2/2004 | McFadden et al. | |

FOREIGN PATENT DOCUMENTS

| | | |
|---|---|---|
| EP | 1034789 A1 | 9/2000 |
| WO | WO 91/16431 | 10/1991 |
| WO | WO 92/17583 | 10/1992 |
| WO | WO 96/33730 | 10/1996 |
| WO | WO 97/11714 | 4/1997 |
| WO | WO 97/44054 | 11/1997 |
| WO | WO 00/12555 | 3/2000 |
| WO | WO 01/07480 | 2/2001 |
| WO | WO 01/62285 | 8/2001 |
| WO | WO 02/031115 | 4/2002 |
| WO | WO 02/32374 | 4/2002 |
| WO | WO 02/046214 | 6/2002 |
| WO | WO 02/060479 | 8/2002 |
| WO | WO 02/092008 | 11/2002 |

OTHER PUBLICATIONS

Ahuja et al., "Chemokine Receptors and Molecular Mimicry," *Immunol. Today* 15:281-287 (1994).
Alcami et al., "Blockade of Chemokine Activity by a Soluble Chemokine Binding Protein from Vaccinia Virus," *J. Immunol.* 160:624-633 (1998).
Alcami et al., "Poxviruses: Capturing Cytokines and Chemokines," *Sem. Virology* 8:419-427 (1998).
Alcami and Smith, "Soluble Interferon-Gamma Receptors Encoded by Poxviruses," *Comp. Immunol. Microbiol. Infect. Dis.* 19:305-317 (1996).
Alcami and Smith, "Vaccinia Cowpox, and Camelpox Viruses Encode Soluble Gamma Interferon Receptors with Novel Broad Species Specificity," *J. Virol.* 69:4633-4639 (1995).
Alcami and Smith, "Receptors for Gamma-Interferon Encoded by Poxviruses: Implications for the Unknown Origin and Vaccina Virus," *Trends Microbiol.* 4:321-326 (1996).
Amano et al., "Identification and Characterization of the Thymidine Kinase Gene of Yaba Virus," *J. Gen. Virol.* 76:1109-1115 (1995).
Barinaga, "Viruses Launch Their Own 'Star Wars'," *Science* 258:1730-1731 (1992).
Born et al., "A Poxvirus Protein that Binds to and Inactivates IL-18, and Inhibits NK Cell Response.," *J. Immunol.* 164:3246-54 (2000).
Brunetti et al., "A Secreted High-Affinity Inhibitor of Human TNF from Tanapox Virus," *Proc. Natl. Acad. Sci. U.S.A.* 100:4831-4836 (2003).
Brunetti et al., "Complete Genomic Sequence and Comparitive Analysis of the Tumorigenic Poxvirus Yaba Monkey Tumor Virus," *J. Virol.* 77:13335-13347 (2003).
Calderara et al., "Orthopoxvirus IL-18 Binding Proteins: Affinities and Antagonist Activities," *Virology* 279: 22-26 (2001).
Chaudhuri et al., "Expression of the Duffy Antigen in K562 Cells. Evidence that it is the Human Erythrocyte Chemokine Receptor," *J. Biol. Chem.* 269:7835-7838 (1994).
Elsner et al., "Eotaxin-2 Activates Chemotaxis-Related Events and Release of Reactive Oxygen Species via Pertussis Toxin-Sensitive G Proteins in Human Eosinophils," *Eur. J. Immunol.* 28:2152-2158 (1998).
Endres et al., "CD4-Independent Infection by HIV-2 is Mediated by Fusin/CXCR4," *Cell* 87:745-746 (1996).

(Continued)

*Primary Examiner*—Ali R. Salimi
(74) *Attorney, Agent, or Firm*—Clark & Elbing LLP; Kristina Bieker-Brady

(57) ABSTRACT

The invention generally features the use of Yaba monkey tumor virus nucleic acid molecules and polypeptides for the treatment or prevention of immunoinflammatory disorders.

53 Claims, 6 Drawing Sheets

OTHER PUBLICATIONS

Essani et al., "Multiple Anti-Cytokine Activities Secreted from Tanapox Virus-Infected Cells," *Microb. Pathog.* 17:347-353 (1994).

Esteban and Buller, "Identification of Residues in an Orthopoxvirus Interleukin-18 Binding Protein Involved in Ligand Binding and Species Specificity," *Virology* 323:197-207 (2004).

Esteban et al., "Interleukin-18 and Glycosaminoglycan Binding by a Protein Encoded by Variola Virus," *J. Gen. Virol.* 85:1291-1299 (2004).

Fenger and Rouhandeh, "Proteins of Yaba Monkey Tumor Virus I. Structural Proteins," *J. Virol.* 18:757-764 (1976).

Gene Bank Sequence, AB015885.
Gene Bank Sequence, AB018404.
Gene Bank Sequence, AB025319.
Gene Bank Sequence, AF153912.
Gene Bank Sequence, AJ293568.
Gene Bank Sequence, AY253324.
Gene Bank Sequence, D26580.

Graham et al., "Myxoma Virus M11L ORF Encodes a Protein for Which Cell Surface Localization is Critical in Manifestation of Viral Virulence," *Virology* 191:112-124 (1992).

Graham et al., "The T1/35kDa Family of Poxvirus-Secreted Proteins Bind Chemokines and Modulate Leukocyte Influx into Virus-Infected Tissues," *Virology* 229:12-24 (1997).

Hoffman and Karpus, "Chemokine Regulation of CNS T-Cell Infiltration in Experimental Autoimmune Encephalomyelitis," *Res. Immunol.* 149:790-794(1998).

Horuk, "Molecular Properties of the Chemokine Receptor Family," *Trends Pharmacol. Sci.* 15:159-165 (1994).

Hu et al., "Cowpox Virus Contains Two Copies of an Early Gene Encoding a Soluble Secreted Form of the Type II TNF Receptor," *Virology* 204:343-356 (1994).

Jackson et al., "Expression of Mouse Interleukin-4 by a Recombinant Ectromelia Virus Suppresses Cytolytic Lymphocyte Responses and Overcomes Genetic Resistance to Mousepox," *J. Virol.* 75:1205-1210 (2001).

Knight et al., "Studies on Tanapox Virus," *Virology* 172:116-124 (1989).

Kotwal and Jayaraman, "Regulation of Cytokine Secretion by Poxvirus Encoded Proteins," *Adv. Exp. Med. Biol.* 351:187(1992).

Lee et al., "The Genome Sequence of Yaba-Like Disease Virus, a Yatapoxvirus," *Virology* 281:170-192 (2001).

Lee and Smith, "The Sequence of Yaba-Like Disease Virus, A Yatapoxvirus," XIII$^{th}$ International Poxvirus-Iridovirus Symposium, Sep. 2-6, 2000.

Lee et al., "Studies of Yaba-Like Disease Virus, a Yatapoxvirus," *University of Oxford, Thesis*, pp. 15-27 and 191-239 (Sep. 25, 2000).

Lomas et al., "Inhibition of Plasmin, Urokinase, Tissue Plasminogen Activator, and $C_{1S}$ by a Myxoma Virus Serine Proteinase Inhibitor," *J. Biol. Chem.* 268:516-521 (1993).

Macen et al., "SERP1, a Serine Proteinase Inhibitor Encoded by Myxoma Virus, is a Secreted Glycoprotein that Interferes with Inflammation," *Virology* 195:348-363 (1993).

McFadden, "Rabbit, Hare, Squirrel and Swine Poxviruses," *Encyclopedia of Virology* pp. 1153-1160 (1997).

McFadden et al., "Myxoma T2 Proteins as a Model for Poxvirus TNF Receptor Homologs," *J. Neuroimmunol.* 72:119-126 (1997).

McFadden et al., "Interruption of Cytokine Networks by Poxviruses: Lessons from Myxoma Virus," *J. Leukocyte Biol.* 57:731-738 (1995).

Moss et al., "Immune-Defense Molecules of Molluscum Contagiosum Virus, a Human Poxvirus," *Trends Microbiol.* 8:473-477 (2000).

Mossman et al., "Myxoma Virus M-T7, a Secreted Homolog of the Interferon-Gamma Receptor, is a Critical Virulence Factor for the Development of Myxomatosis in European Rabbits," *Virology* 215:17-30 (1996).

Mossman et al., "Species Specificity of Ectromelia Virus and Vaccinia Virus Interferon-Gamma Binding Proteins," *Virology* 208:762-769 (1995).

Mossman et al., "The Myxoma Virus-Soluble Interferon-γ Receptor Homolog, M-T7, Inhibits Interferon-γ in a Species-Specific Manner," *J. Biol. Chem.* 270:3031-3038 (1995).

Mossman et al., "Interferon-Gamma Receptors Encoded by Poxviruses," *Viroreceptor, Virokines And Related Immune Modulators Encoded by DNA Viruses*, Ed: McFadden, R.G. Landers Co., Chapter 4, pp. 41-54 (1994).

Neote et al., "Molecular Cloning, Functional Expression, and Signaling Characteristics of a C-C Chemokine Receptor," *Cell* 72:415-425 (1993).

Neurath et al., "Search for Hepatitis B Virus Cell Receptors Reveals Binding Sites for Interleukin 6 on the Virus Envelope Protein," *J. Exp. Med.* 175:461-469 (1992).

Olsen and Yohn, "Immunodiffusion Analysis of Yaba Poxvirus Structural and Associated Antigens," *J. Virol.* 5:212-220 (1970).

Opgenorth et al., "Deletion of the Growth Factor Gene Related to EGF and TGFα Reduces Virulence of Malignant Rabbit Fibroma Virus," *Virology* 186:175-191 (1992).

Opgenorth et al., "Deletion Analysis of Two Tandemly Arranged Virulence Genes in Myxoma Virus, M11L and Myxoma Growth Factor," *J. Virol.* 66:4720-4731 (1992).

Opgenorth et al., "Transforming Growth Factor Alpha, Shope Fibroma Growth Factor, and Vaccinia Growth Factor can Replace Myxoma Growth Factor in the Induction of Myxomatosis in Rabbits," *Virology* 192:701-709 (1993).

Paulose et al., "Selective Inhibition of a TNF-α Induced Cell Adhesion Molecule Gene Expression by Tanapox Virus," *Microb. Pathog.* 25:33-41 (1998).

Powell et al., "An I-Kappa-B Homolog Encoded by African Swine Fever Virus Provides a Novel Mechanism for Downregulation of Proinflammatory Cytokine Responses in Host Macrophages," *J. Virol.* 70:8527-8533 (1996).

Riffkin et al., "A Single Amino-Acid Change Between the Antigenically Different Extracellular Serine Proteases V2 and B2 from *Dichelobacter nodosus*," *Gene* 167:279-283 (1995).

Schreiber and McFadden, "The Myxoma Virus TNF-Receptor Homologue (T2) Inhibits Tumor Necrosis Factor-Alpha in a Species-Specific Fashion," *Virololgy* 204:692-705 (1994).

Sedger and McFadden, "M-T2: A Poxvirus TNF Receptor Homologue with Dual Activities," *Immunol. Cell Biol.* 74:538-545 (1996).

Senkevich et al., "Genome Sequence of a Human Tumorigenic Poxvirus: Prediction of Specific Host Response-Evasion Genes," *Science* 273:813-816 (1996).

Senkevich et al., "The Genome of Molluscum Contagiosum Virus: Analysis and Comparison with Other Poxviruses," *Virology* 233:19-42 (1997).

Smith et al., "Ectromelia, Vaccinia and Cowpox Viruses Encode Secreted Interleukin-18-Binding Proteins," *J. Gen. Virol.* 81:1223-1230 (2000).

Smith et al., "T2 Open Reading Frame From the Shope Fibroma Virus Encodes a Soluble Form of the TNF Receptor," *Biochem. Biophys. Res. Commun.* 176:335-342 (1991).

Smith, "Virus Proteins that Bind Cytokines, Chemokines, or Interferons," *Curr. Opin. Immunol.* 8:467-471 (1996).

Symons et al., "The Vaccinia Virus C12L Protein Inhibits Mouse IL-18 and Promotes Virus Virulence in the Murine Intranasal Model," *J. Gen. Virol.* 83:2833-44 (2002).

Symons et al., "Vaccinia Virus Encodes a Soluble Type I Interferon Receptor of Novel Structure and Broad Species Specificity," *Cell* 81:551-560 (1995).

Thompson, "Human Gene Therapy Harsh Lessons, High Hopes," *FDA Consum.* 34:19-24 (2000).

Trkola et al., "CD4-Dependent, Antibody-Sensitive Interactions Between HIV-1 and Its Co-Receptor CCR-5," *Nature* 384:184-187 (1996).

Upton et al., "Tumorigenic Poxviruses: Genomic Organization and DNA Sequence of the Telomeric Region of the Shope Fibroma Virus Genome," *Virology* 160:20-30 (1987).

Upton et al., "Myxoma Virus Expresses a Secreted Protein with Homology to the Tumor Necrosis Factor Receptor Gene Family that Contributes to a Viral Virulence," *Virology* 184:370-382 (1991).

Upton et al., "Encoding of a Homolog of the IFN-Gamma Receptor by Myxoma Virus," *Science* 258:1369-1372 (1992).

Upton et al., "Mapping and Sequence of a Gene from Myxoma Virus That is Related to Those Encoding Epidermal Growth Factor and Transforming Growth Facter Alpha," *J. Virol.* 61:1271-1275 (1987).

Upton et al., "Myxoma Virus and Malignant Rabbit Fibroma Virus Encode a Serpin-Like Protein Important for Virus Virulence," *Virology* 179:618-631 (1990).

Upton and McFadden, "Detection of Viral Homologs of Cellular Interferon Gamma Receptors," *Methods in Molecular Genetics* 4:383-390, Molecular Virology Techniques Part A, Ed: Adolph, Academic Press Inc. (1994).

Vinyals et al., "Failure of Wild-Type p53 Gene Therapy in Human Cancer Cells Expressing a Mutant p53 Protein," *Gene Ther.* 6:22-33 (1999).

Xiang and Moss, "Correspondence of the Functional Epitopes of Poxvirus and Human Interleukin-18-Binding Proteins," *J. Virol.* 75:9947-9954 (2001).

Xiang and Moss, "Determination of the Functional Epitopes of Human Interleukin-18-Binding Protein by Site-Directed Mutagenesis," *J. Biol. Chem.* 276:17380-17386 (2001).

Xiang and Moss, "Identification of Human and Mouse Homologs of the MC51L-53L-54L Family of Secreted Glycoproteins Encoded by the Molluscum Contagoisum Poxvirus," *Virology* 257:297-302 (1999).

Xiang and Moss, "IL-18 Binding and Inhibition of Interferon Gamma Induction by Human Poxvirus-Encoded Proteins," *Proc. Natl. Acad. Sci. U.S.A.* 96:11537-11542 (1999).

Xiang and Moss, "Molluscum Contagiosum Virus Interleukin-18 (IL-18) Binding Protein is Secreted as a Full-Length Form That Binds Cell Surface Glycosaminoglycans Through the C-Terminal Tail and a Furin-Cleaved Form with Only the IL-18 Binding Domain," *J. Virol.* 77:2623-30 (2003).

Wu et al., "CD4-Induced Interaction of Primary HIV-1 gp120 Glycoproteins with the Chemokine Receptor CCR-5," *Nature* 384:179-183 (1986).

International Search Report for WO 02/031115 dated Mar. 15, 2002.

International Search Report for WO 02/046214 dated May 3, 2002.

McFadden and Murphy, "Host-Related Immunomodulators Encoded by Poxviruses and Herpesviruses," *Curr. Opin. Microbiol.* 3(4):371-378 (2000).

Nazarian et al., "Yaba Monkey Tumor Virus Encodes a Functional Inhibitor of Interleukin-18," *J. Virol.* 82(1):522-8 (2008). [Epub 2007 Oct 24.].

Aizawa et al., "Cloning and Expression of Interleukin-18 Binding Protein," *FEBS Lett.* 445(2-3):338-342 (1999).

Kim et al., "Structural Requirements of Six Naturally Occurring Isoforms of the IL-18 Binding Protein to Inhibit IL-18," *Proc. Natl. Acad. Sci.* USA 97(3):1190-1195 (2000).

Massung et al., "DNA Sequence Analysis of Conserved and Unique Regions of Swinepox Virus: Identification of Genetic Elements Supporting Phenotypic Observations Including a Novel G Protein-Coupled Receptor Homologue," *Virology* 197(2):511-528 (1993).

Nazarian et al., "Comparative Genetic Analysis of Genomic DNA Sequences of Two Human Isolates of Tanapox Virus," *Virus Res.* 129(1):11-25 (2007).

Novick et al., "Interleukin-18 Binding Protein: a Novel Modulator of the Th1 Cytokine Response," *Immunity* 10(1):127-136 (1999).

Watanabe et al., "Evolution of Interleukin-18 Binding Proteins and Interleukin-1 Receptor, Type II Proteins," *Int. J. Mol. Med.* 15(4):561-566 (2005).

* cited by examiner

Figure 1A

```
atgaaaaaaa ttgcaattat tttgtttttg ttgagttttt gtttttcatg tgacggtgaa  60
aaagaatgcg ataagcatag aagcgttaat attcaagttc cgatgaaaga aactagcgag 120
gtgttgttaa ggtgtaccgg tagttcgtat tttaagcatt ttagttatgt ttactggctt 180
gtgggagaaa gcgaaaccgt agatcagttg caacaaaatt ccggatatgg tgaaaccagt 240
caccctttcaa aacctcacga gtgtggaaac ttacctagcg ccgatttagt tctgacgaat 300
atgacagaaa aaatgcgtga cacaaagttg acttgtgtgt taatggaccc agacggacac 360
attgacgaat ctttagtatt acgcgaagtg tgggattgtt taacaaaac a            411
```

Figure 1B

```
Met Lys Lys Ile Ala Ile Ile Leu Phe Leu Leu Ser Phe Cys Phe Ser
 1               5                  10                  15
Cys Asp Gly Glu Lys Glu Cys Asp Lys His Arg Ser Val Asn Ile Gln
                20                  25                  30
Val Pro Met Lys Glu Thr Ser Glu Val Leu Leu Arg Cys Thr Gly Ser
            35                  40                  45
Ser Tyr Phe Lys His Phe Ser Tyr Val Tyr Trp Leu Val Gly Glu Ser
        50                  55                  60
Glu Thr Val Asp Gln Leu Gln Gln Asn Ser Gly Tyr Gly Glu Thr Ser
65                  70                  75                  80
His Pro Ser Lys Pro His Glu Cys Gly Asn Leu Pro Ser Ala Asp Leu
                85                  90                  95
Val Leu Thr Asn Met Thr Glu Lys Met Arg Asp Thr Lys Leu Thr Cys
                100                 105                 110
Val Leu Met Asp Pro Asp Gly His Ile Asp Glu Ser Leu Val Leu Arg
            115                 120                 125
Glu Val Trp Asp Cys Phe Asn Lys Thr
        130                 135
```

IMMUNOMODULATORY PROTEIN AND USEFUL EMBODIMENTS THEREOF

CROSS REFERENCE TO RELATED APPLICATIONS

This application is a continuation-in-part of U.S. Ser. No. 10/455,000, filed Jun. 4, 2003, which is a continuation-in-part of International Application No. PCT/CA01/01734, filed Dec. 4, 2001, published in English under PCT article 21(2), which claims benefit of U.S. provisional application 60/251,147, filed Dec. 4, 2000, each of which is hereby incorporated by reference.

FIELD OF THE INVENTION

This invention relates to a novel secreted viral protein that may be utilized in the treatment of human diseases.

BACKGROUND OF THE INVENTION

Poxviruses are a large family of DNA viruses known to infect a variety of mammalian species. To date, approximately 50 poxvirus genomes have been identified and each genome contains about 200 open reading frames encoded therein. The poxvirus family, otherwise known as Poxviridae, includes two subfamilies (Chordopoxvirinae and Entomopoxvirinae) wherein the species are divided into eight and three genuses respectively, including but not limited to Orthopoxvirus, Parapoxvirus, Avipoxvirus, Capripoxvirus, Leporipoxvirus, Suipoxvirus, Molluscipoxvirus and Yatapoxvirus, which include but are not limited to the species known as Myxoma Virus, Vaccinia Virus, Swinepox Virus, Molluscum Contagiosum Virus and Yaba Monkey Tumor Virus. Poxviruses are characterized as large, brick-like virions with complex symmetry that share antigenic determinants among different species of the family.

It is well known within the art that, upon infection of a host organism, the poxvirus genome mediates expression of numerous proteins that interfere with and modulate homeostasis within the host. In addition to proteins that mediate an intracellular effect, poxviruses are also known to secrete proteins into the circulatory system of the infected animal. Such secreted proteins include agents that bind and inhibit various different aspects of the mammalian immune system and minimize immune-mediated clearance of the virus.

The Yaba Monkey Tumor Virus (YMTV) is a poxvirus of the Yatavirus genus and was characterized in 1958 during outbreaks of rhesus monkeys. YMTV infection in monkeys leads to epidermal histiocytomas that advance to suppurative inflammatory reactions. Related poxvirus family members include Tanapoxvirus (TPV) and Yaba-like Disease Virus (YLDV).

YMTV has a DNA genome of 136 kilobase. YMTV grows relatively slowly in primate cell culture lines and its host range is restricted to a small number of primates, and occasionally man following accidental exposure to infected monkeys.

IL-18 is a pro-inflammatory mammalian cytokine that plays an important early function in the potentiation of $T_h1$-like immune responses. In addition to its independent effects, IL-18 synergizes with IL-12 to induce IFN-γ production from various immune cell types. Binding of IL-18 to specific cell-surface receptors induces NF-κB activation and IL-18 is important in vivo for production of IFN-γ and inflammatory responses that may contribute to inflammatory disease. These diseases include but are not limited to allergic inflammation, atherosclerotic plaque growth and unstable plaque rupture, arterial restenosis, by-pass graft occlusion, Gaucher's disease, diabetes mellitus, rheumatoid arthritis, multiple sclerosis, transplant rejection, transplant vasculopathy and glomerulonephritis.

SUMMARY OF THE INVENTION

This invention provides the non-obvious identification and characterization of a protein derived from YMTV, called YMTV Cytokine Inhibitor, or YCI. The invention embodies YCI nucleic acid molecules and polypeptides and methods of detecting and producing YCI. The invention further embodies the use of a YCI polypeptide or a nucleic acid molecule for modulating the immune response within an organism or a cell. It is further claimed herein that the YCI polypeptides or nucleic acid molecules can be utilized for the purpose of preventing, treating, or reversing the onset of one or more immune-related diseases, including but not limited to inflammation and the immune-mediated diseases outlined herein.

Accordingly, in a first aspect, the invention features a method for treating a subject diagnosed with or at risk of developing an immunoinflammatory disorder that includes administering to the subject a purified YCI polypeptide, or a fragment or derivative thereof, in an amount and for a time sufficient to treat the subject. The YCI polypeptide is any YCI polypeptide that includes a sequence substantially identical to at least a fragment of SEQ ID NO: 2, preferably a sequence that is at least 85%, 90%, 95%, 96%, 97%, 98%, 99%, or 100% identical to the sequence of SEQ ID NO: 2 or at least 85%, 90%, 95%, 96%, 97%, 98%, 99%, or 100% identical to amino acids 20-137 of SEQ ID NO: 2.

In preferred embodiments, the YCI polypeptide, or fragment or derivative thereof, has YCI biological activity including, but not limited, to the ability to bind to a cytokine, preferably IL-18; the ability to sequester the cytokine; or the ability to inhibit the activity of the cytokine (e.g., binding to IL-18 receptor or induction of IFN-γ), or both.

In another aspect, the invention features a method for treating a subject diagnosed with or at risk of developing an immunoinflammatory disorder that includes administering to the subject a purified YCI nucleic acid molecule, or a fragment or derivative thereof, in an amount and for a time sufficient to treat the subject. The YCI nucleic acid molecule includes any nucleic acid molecule having a sequence substantially identical to at least a fragment of SEQ ID NO: 1, preferably 85%, 90%, 95%, 96%, 97%, 98%, 99%, or 100% identical to the sequence of SEQ ID NO: 1, and encodes a YCI polypeptide. In preferred embodiments, the YCI nucleic acid molecule encodes a YCI polypeptide that has YCI biological activity including, but not limited to, the ability to bind to a cytokine, preferably IL-18. In preferred embodiments, the encoded YCI polypeptide can bind to and sequester the cytokine or inhibit the activity of the cytokine, or both.

In another aspect the invention features a pharmaceutical composition that includes a purified YCI polypeptide, or fragment or derivative thereof, that is substantially identical to at least a fragment of SEQ ID NO: 2, formulated in a pharmaceutically acceptable carrier in an amount sufficient to treat an immunoinflammatory disorder when administered to a subject. The YCI polypeptide is preferably 85%, 90%, 95%, 96%, 97%, 98%, 99%, or 100% identical to the sequence of SEQ ID NO: 2 or 85%, 90%, 95%, 96%, 97%, 98%, 99%, or 100% identical to amino acids 20-137 of SEQ ID NO: 2. The YCI polypeptide can also any homolog, analog, or derivative thereof, preferably one that is virally encoded. In preferred embodiments, the YCI polypeptide has YCI biological activity including but not limited to the ability to bind to a cytokine, preferably IL-18. In preferred embodiments, the YCI polypeptide can bind to and sequester the cytokine or inhibit the activity of the cytokine, or both.

In another aspect, the invention features a kit that includes a purified YCI polypeptide, or fragment or derivative thereof, that is substantially identical to at least a fragment of SEQ ID NO: 2, and instructions for administering the polypeptide to a subject diagnosed with or at risk of developing an immunoinflammatory disorder. The YCI polypeptide is preferably 85%, 90%, 95%, 96%, 97%, 98%, 99%, or 100% identical to the sequence of SEQ ID NO: 2 or 85%, 90%, 95%, 96%, 97%, 98%, 99%, or 100% identical to amino acids 20-137 of SEQ ID NO: 2. In preferred embodiments, the YCI polypeptide has YCI biological activity including but not limited to the ability to bind to a cytokine, preferably IL-18. In preferred embodiments, the YCI polypeptide can bind to and sequester the cytokine or inhibit the activity of the cytokine, or both.

The immunoinflammatory disorders that are treated or prevented by any of the methods or compositions of the invention include, but are not limited to, acute inflammation, rheumatoid arthritis, transplant rejection, transplant vasculopathy, asthma, allergic inflammation, arterial restenosis, by-pass graft occlusion, Guacher's disease, inflammatory bowel disease, uveitis, restenosis, multiple sclerosis, psoriasis, wound healing, lupus erythematosus, allergic rhinitis, atopic dermatitis, food allergies, diabetes, including type 1 insulin-dependent diabetes mellitus, deramatitis, meningitis, colitis, thrombotic thrombocytopenic purpura, Sjogren's syndrome, encephalitis, leukocyte adhesion deficiency, rheumatic fever, Reiter's syndrome, psoriatic arthritic, osteoarthritis, ocular inflammatory disorders, progressive systemic sclerosis, primary biliary cirrhosis, pemphigus, pemphigoid, necrotizing vasculitis, mayasthenia gravis, lupus erythmatosus, polymyositis, sarcoidosis, granulomatorsis, vasculitis, pernicious anemia, CNS inflammatory disorder, antigen-antibody complex mediated diseases, autoimmune hemolytic anemia, Hashimoto's thyroiditis, Graves disease, habitual spontaneous abortions, Reynard's syndrome, glomerulonephritis, dermatomyositis, chromic active hepatitis, celiac disease, autoimmune complications of AIDS, atrophic gastritis, ankylosing spondylitis, Addison's disease, psoriasis, penphigus vularis, Behcet's syndrome, acute respiratory distress syndrome (ARDS), ischemic heart disease, atherosclerosis, post-dialysis syndrome, leukemia, acquired immune deficiency syndrome, septic shock, lipid histiocytosis, or cancer.

In another aspect, the invention features a method of modulating cytokine function in a cell that includes contacting the cell with a purified YCI polypeptide that is substantially identical to at least a fragment of SEQ ID NO: 2, in an amount and for a time sufficient to modulate cytokine function in the cell. The YCI polypeptide is preferably 85%, 90%, 95%, 96%, 97%, 98%, 99%, or 100% identical to the sequence of SEQ ID NO: 2 or 85%, 90%, 95%, 96%, 97%, 98%, 99%, or 100% identical to amino acids 20-137 of SEQ ID NO: 2. The YCI polypeptide can also any homolog, analog, or derivative thereof, preferably one that is virally encoded. In preferred embodiments, the cytokine is any cytokine or chemokine, preferably IL-18. In preferred embodiments, the YCI polypeptide can bind to and sequester the cytokine or inhibit the activity of the cytokine, or both.

In another aspect, the invention features a method of modulating cytokine function in a cell that includes contacting the cell with a purified YCI nucleic acid molecule, or fragment or derivative thereof, that is substantially identical to at least a fragment of SEQ ID NO: 1 in an amount and for a time sufficient to modulate cytokine function in the cell. The YCI nucleic acid molecule is preferably 85%, 90%, 95%, 96%, 97%, 98%, 99%, or 100% identical to the sequence of SEQ ID NO: 1 and encodes a YCI polypeptide. In preferred embodiments, the cytokine is any cytokine or chemokine, preferably IL-18. In preferred embodiments, the YCI nucleic acid molecule encodes a polypeptide that can bind to and sequester the cytokine or inhibit the activity of the cytokine, or both.

By "an amount sufficient" is meant the amount of a compound, in a combination of the invention, required to treat or prevent an immunoinflammatory disease in a clinically relevant manner. A sufficient amount of an active compound used to practice the present invention for therapeutic treatment of conditions caused by or contributing to an immunoinflammatory disease varies depending upon the manner of administration, the age, body weight, and general health of the patient. Ultimately, the prescribers will decide the appropriate amount and dosage regimen.

The term "antibody" refers to protein molecules derived from a polyclonal or monoclonal population of B cells of mammalian origin. The term "antibody fragment" refers to the aforementioned antibody molecules that have been cleaved into different segments and/or may be labeled with fluorochrome compounds for the purpose of detection.

By "binding" is meant a non-covalent or a covalent interaction, preferably non-covalent, that holds two molecules together. For example, two such molecules could be a ligand and its receptor, an enzyme and an inhibitor of that enzyme, an enzyme and its substrate, or an antibody and an antigen. Non-covalent interactions include, but are not limited to, hydrogen bonding, ionic interactions among charged groups, van der Waals interactions, and hydrophobic interactions among non-polar groups. One or more of these interactions can mediate the binding of two molecules to each other. Binding may exhibit discriminatory properties such as specificity or selectivity.

The term "cytokine" refers to all mammalian, preferably human, cytokines known within the art that bind extracellular receptors upon the cell surface and thereby modulate cell function, including but not limited to IL-1, IL-4, IL-6, IL-18, TNF-α, and IFN-γ. Cytokines are released by cells of the immune system and act as intracellular modulators in the generation of an immune response. Also included in this definition are chemokines. The term "chemokine" refers to all known chemotactic cytokines expressed within mammalian organisms that mediate the recruitment and infiltration of leukocytes into tissues. The term "chemokine" includes but is not limited to all mammalian members of the C, CC, CXC, and CXXXC families of chemotactic cytokines, classified within the art based upon the distribution of cysteine residues therein. The term "chemokine receptor" refers to all known transmembrane proteins known within the art to interact with one or more chemokines.

The term "cytokine receptor" refers to all mammalian, preferably human, cytokine receptors within the art that bind one or more cytokine(s), including but not limited to receptors of IL-1, IL-4, IL-6, IL-18, TNF-α and IFN-γ. The term "chemokine receptor" shall include but is not limited to all chemokine receptors classified within the art as CR, CCR, CXCR and CXXXCR.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, or 100, 150, 200, 250, 300, 350, 400, 411 or more nucleotides up to the entire length of the nucleic acid molecule or 10, 20, 30, 40, 50, 60, 70, 80, 90, 100, 100, 110, 120, 130, or 137 amino acids or more up to the entire length of the nucleic acid molecule. Preferred fragments of YCI will have YCI biological activity (e.g., binding to cytokines such as IL-18) and may include, for example, the IL-18 binding domain.

By "heterologous" is meant any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

By "homolog" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 55%, 57%, 60%, 65%, 68%, 70%, more preferably 80% or 85%, and most preferably 90%, 95%, 98%, or 99% identical at the amino acid level or nucleic acid to a reference sequence. For polypeptides, the length of comparison sequences will generally be at least or 10, 20, 30, 40, 50, 60, 70, 80, 90, 100, 100, 110, 120, 130, or 137 amino acids or more. For nucleic acids, the length of comparison sequences will generally be at least 10, 20, 30, 40, 50, 60, 70, 80, 90, or 100, 150, 200, 250, 300, 350, 400, 411 or more nucleotides. Preferred homologs include homologous polypeptides or nucleic acid molecules from the other members of the Yata genus of poxviruses including tanapoxvirus (TPV) and Yaba-like disease virus (YLDV).

By "hybridize" is meant pair to form a double-stranded molecule between complementary polynucleotide, or portions thereof, under various conditions of stringency. (See, e.g., Wahl, G. M. and S. L. Berger (1987) *Methods Enzymol.* 152:399; Kimmel, A. R. (1987) *Methods Enzymol.* 152:507) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci., USA* 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acute inflammation, rheumatoid arthritis, transplant rejection, transplant vasculopathy, asthma, allergic inflammation, arterial restenosis, by-pass graft occlusion, Guacher's disease, inflammatory bowel disease, uveitis, restenosis, multiple sclerosis, psoriasis, wound healing, lupus erythematosus, allergic rhinitis, atopic dermatitis, food allergies, diabetes, including type 1 insulin-dependent diabetes mellitus, deramatitis, meningitis, colitis, thrombotic thrombocytopenic purpura, Sjogren's syndrome, encephalitis, leukocyte adhesion deficiency, rheumatic fever, Reiter's syndrome, psoriatic arthritic, osteoarthritis, ocular inflammatory disorders, progressive systemic sclerosis, primary biliary cirrhosis, pemphigus, pemphigoid, necrotizing vasculitis, mayasthenia gravis, lupus erythmatosus, polymyositis, sarcoidosis, granulomatorsis, vasculitis, pernicious anemia, CNS inflammatory disorder, antigen-antibody complex mediated diseases, autoimmune hemolytic anemia, Hashimoto's thyroiditis, Graves disease, habitual spontaneous abortions, Reynard's syndrome, glomerulonephritis, dermatomyositis, chromic active hepatitis, celiac disease, autoimmune complications of AIDS, atrophic gastritis, ankylosing spondylitis, Addison's disease, psoriasis, penphigus vularis, Behcet's syndrome, acute respiratory distress syndrome (ARDS), ischemic heart disease, atherosclerosis, post-dialysis syndrome, leukemia, acquired immune deficiency syndrome, septic shock, lipid histiocytosis, and cancer.

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline.

Other physiologically acceptable carriers and their formulations are known to one skilled in the art and described, for example, in Remington's Pharmaceutical Sciences, (20$^{th}$ edition), ed. A. Gennaro, 2000, Lippincott, Williams & Wilkins, Philadelphia, Pa.

By "preventing" is meant prophylactic treatment of a subject who is not yet ill, but who is susceptible to, or otherwise at risk of, developing a particular disease. Preferably a subject is determined to be at risk of developing an immunoinflammatory disorder using diagnostic methods known in the art.

By "protein," "polypeptide," or "peptide" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "purified" is meant separated from other components that naturally accompany it. Typically, a compound (e.g., nucleic acid, polypeptide, small molecule) is substantially pure when it is at least 50%, by weight, free from proteins, antibodies, and naturally-occurring organic molecules with which it is naturally associated. Preferably, the factor is at least 75%, more preferably, at least 90%, and most preferably, at least 99%, by weight, pure. A substantially pure factor may be obtained by chemical synthesis, separation of the factor from natural sources, or production of the factor in a recombinant host cell that does not naturally produce the factor. Proteins and small molecules may be purified by one skilled in the art using standard techniques such as those described by Ausubel et al. (Current Protocols in Molecular Biology, John Wiley & Sons, New York, 2000). The factor is preferably at least 2, 5, or 10 times as pure as the starting material, as measured using polyacrylamide gel electrophoresis, column chromatography, optical density, HPLC analysis, or western analysis (Ausubel et al., supra). Preferred methods of purification include immunoprecipitation, column chromatography such as immunoaffinity chromatography, magnetic bead immunoaffinity purification, and panning with a plate-bound antibody.

By "subject" is meant a mammal, including, but not limited to, a human or non-human mammal, such as a bovine, equine, canine, ovine, or feline.

By "substantially identical" is meant a nucleic acid or amino acid sequence that, when optimally aligned, for example using the methods described below, share at least 60%, 65%, preferably 70%, 75%, 80%, 85%, 90%, 95%, 96%, 97%, 98%, 99%, or 100% sequence identity with a second nucleic acid or amino acid sequence, e.g., a YCI nucleic acid or amino acid sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith and Waterman *J. Mol. Biol.* 147:195-7, 1981); "Best-Fit" (Smith and Waterman, Advances in Applied Mathematics, 482-489, 1981) as incorporated into GeneMatcher Plus™, Schwarz and Dayhof "Atlas of Protein Sequence and Structure," Dayhof, M. O., Ed pp 353-358, 1979; BLAST program (Basic Local Alignment Search Tool; (Altschul, S. F., W. Gish, et al., *J. Mol. Biol.* 215: 403-410, 1990), BLAST-2, BLAST-P, BLAST-N, BLAST-X, WU-BLAST-2, ALIGN, ALIGN-2, CLUSTAL, or Megalign (DNASTAR) software.

In addition, those skilled in the art can determine appropriate parameters for measuring alignment, including any algorithms needed to achieve maximal alignment over the length of the sequences being compared. For polypeptides, the length of comparison sequences will generally be at least or 10, 20, 30, 40, 50, 60, 70, 80, 90, 100, 100, 110, 120, 130, or 137 amino acids or more up to the entire length of the polypeptide. For nucleic acids, the length of comparison sequences will generally be at least 10, 20, 30, 40, 50, 60, 70, 80, 90, or 100, 150, 200, 250, 300, 350, 400, 411 or more nucleotides up to the entire length of the nucleic acid molecule. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "sustained release" or "controlled release" is meant that the therapeutically active component is released from the formulation at a controlled rate such that therapeutically beneficial blood levels (but below toxic levels) of the component are maintained over an extended period of time ranging from e.g., about 12 to about 24 hours, thus, providing, for example, a 12 hour or a 24 hour dosage form.

By "treating" is meant administering or prescribing a compound or a pharmaceutical composition for prophylactic and/or therapeutic purposes or administering treatment to a subject already suffering from a disease to improve the subject's condition or to a subject who is at risk of developing a disease. By "treating an immunoinflammatory disorder" is meant that the disorder and the symptoms associated with the disorder are alleviated, reduced, cured, or placed in a state of remission. More specifically, when YCI, or fragments or derivatives thereof, are used to treat a subject with an immunoinflammatory disorder, it is generally provided in a therapeutically effective amount to achieve any one or more of the following: a reduction in the level of inflammatory cytokines (e.g., IL-18, IFNγ, TNFα, and IL-12), a reduction in the levels of activated inflammatory cells (e.g., macrophages, monocytes, T-cells, B-cells), and a reduction in the accumulation of inflammatory cells s sites of inflammation, injury, or disease.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

By "YCI polypeptide" or "YMTV IL-18 bp" is meant a polypeptide having an amino acid sequence that is at least 60%, preferably 70%, 80%, most preferably 85%, 90%, 9%%, 96%, 97%, 98%, 99% or 100% identical over the length of the entire polypeptide to the amino acid sequence set forth in SEQ ID NO: 2. Also included in the definition are fragments of the YCI polypeptide having at least at least 60%, preferably 70%, 80%, most preferably 85%, 90%, 95%, 96%, 97%, 98%, 99% or 100% identity over the length of the fragment to the amino acid sequence set forth in SEQ ID NO: 2 and that have YCI biological activity. Most desirably, the YCI polypeptide includes the sequence set forth in SEQ ID NO: 2 or amino acids 20 to 137 of the sequence set forth in SEQ ID NO: 2, which make up the mature form of the protein lacking the N-terminal signal sequence. Also included are any derivatives of or modifications to the YCI polypeptide including but not limited to the modifications described herein. In one example, amino acids 1-19 (the signal sequence) are modified or replaced to improve expression of the protein.

By "YCI nucleic acid molecule" or "YMTV-14L gene" is meant a nucleic acid molecule that encodes a YCI polypeptide and that is at least 70%, preferably 75%, 80%, most preferably 85%, 90%, 95%, 96%, 97%, 98%, 99% or more identical to the nucleic acid sequences set forth in SEQ ID is NO: 1. Also included in the definition are any nucleic acid molecules having a sequence that differs from SEQ ID NO: 1 by substitution of a T with a U; nucleic acid molecules with sequences complimentary to either the full length of SEQ ID NO: 1, or complimentary to nucleic acid fragments derived thereof; nucleic acid molecules that hybridize with the nucleic acid sequences represented within SEQ ID NO: 1; and nucleic acid molecules that have sequences differing from the full length of SEQ ID NO: 1 due to the degeneracy of the genetic code. The term "nucleic acid" is intended to include DNA and RNA that can either be of single or double stranded structure.

By "YCI biological activity" is meant any one or more of the following activities: binding to a mammalian cytokine, including but not limited to IL-18; sequestering a mammalian cytokine; and inhibiting the biological activity of a mammalian cytokine. Assays for YCI biological activity include cytokine-binding assays, cytokine sequestration assays (for example, as described herein), and assays for the biological activity of a cytokine that are known in the art. Examples of binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. *Anal. Biochem.* 212:457-468 (1993); Schuster et al., *Nature* 365:343-347 (1993)). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR). Additional examples of such assays are known in the art or described herein The following standard abbreviations are utilized throughout specification of the present invention and its included drawings: DNA—deoxyribonucleic acid; RNA—ribonucleic acid; C—cytosine; G—guanine; A—adenosine; T—thymidine; N—unknown; A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and pY, pTyr—phosphotyrosine.

Other features and advantages of the invention will be apparent from the following Detailed Description, the drawings, and the claims.

BRIEF DESCRIPTION OF THE DRAWINGS

The present invention will be further understood and supported using the following drawings and their associated descriptions. These descriptions and drawings are not meant to limit the invention by any circumstance and are to be interpreted as possible embodiments of the invention disclosed herein. The methods utilized in the generation of the data represented by these drawings are commonly known within the art and may be reproduced identically by employing the methods described herein.

FIG. 1 illustrates the genomic nucleic acid sequence of the YCI gene within YMTV (SEQ ID NO: 1) and further illustrates the amino acid sequence of YCI protein expressed by YMTV (SEQ ID NO: 2.)

DETAILED DESCRIPTION OF THE INVENTION

Figure 2:
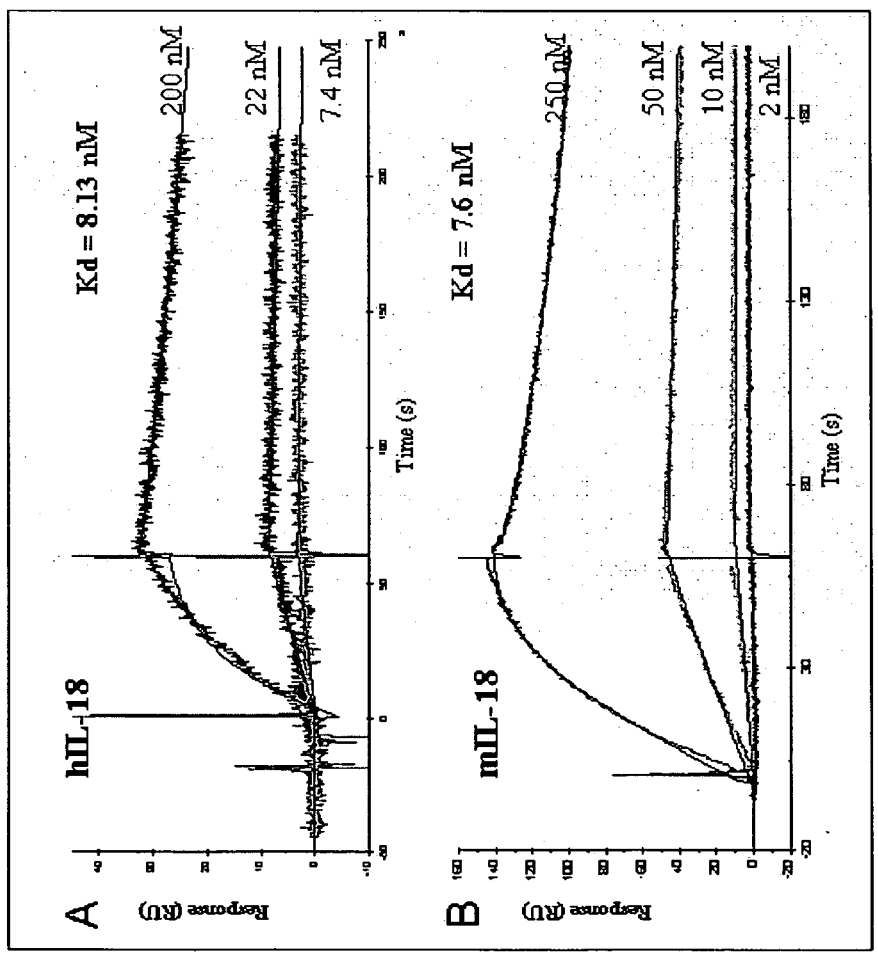
FIGS. 2A-2B are sensograms showing the ability of human (FIG. 2A) and mouse IL-18 (FIG. 2B) to bind to YCI using surface plasmon resonance. Injection of each cytokine was started at 0 seconds and stopped at 60 seconds. Affinity constants are shown in the top right of each panel. Concentrations of each cytokine are labeled at the end of each sensogram.

The invention disclosed herein identifies a novel protein derived from the Yaba Monkey Tumor Virus (YMTV), a member of the poxvirus family, which also includes TPV and YLDV. In particular, this invention discloses an immunomodulatory nucleic acid and amino acid sequence, referred to as YCI, where the nucleic acid sequence and amino acid sequences, including fragments and derivatives thereof, are hereinafter collectively abbreviated as "YCI nucleic acid molecule" or "YCI polypeptide." The YCI gene has a length of 411 nucleotides (SEQ ID NO: 1), corresponding to an amino acid sequence of 137 amino acids (SEQ ID NO: 2). This invention also features the discovery that YCI binds to cytokines, including IL-18, and can sequester and/or inhibit the biological activity of such cytokines. Therefore, the present invention also includes methods of modulating cytokine function and methods and compositions for treating a subject suffering from an immunoinflammatory disorder that include the use of a YCI polypeptide or YCI nucleic acid molecule of the invention.

YCI Polypeptides

YCI polypeptides included in the compositions and methods of the invention include any YCI polypeptide, or fragment or derivative thereof, wherein the polypeptide has an amino acid sequence that is at least 60%, preferably 70%, 80%, most preferably 85%, 90%, 95%, 96%, 97%, 98%, 99% or more identical to the amino acid sequence set forth in SEQ ID NO: 2. In preferred embodiments, the YCI polypeptide also has YCI biological activity. Modifications to the primary structure itself by deletion, addition, or alteration of the amino acids incorporated into the YCI sequence during translation can be made without destroying the activity of the protein. Such modifications can be made to improve expression, stability, solubility, cellular uptake, or biological activity of the protein in the various expression systems. For example, a mutation can increase the binding of the YCI polypeptide to a cytokine, such as IL-18. Generally, substitutions are made conservatively and take into consideration the effect on biological activity. Mutations, deletions, or additions in nucleotide sequences constructed for expression of analog proteins or fragments thereof must, of course, preserve the reading frame of the coding sequences and preferably will not create complementary regions that could hybridize to produce secondary mRNA structures such as loops or hairpins which would adversely affect translation of the mRNA.

YCI is a virally encoded protein but its biological activity, when expressed in mammalian cells, includes binding to mammalian cytokines, including but not limited to IL-18, sequestering mammalian cytokines, and inhibiting the biological activity of mammalian cytokines. Assays for YCI biological activity include cytokine binding assays, cytokine sequestration assays (for example, as described herein), and assays for the biological activity of a cytokine that are known in the art. Examples of binding assays and assays for cytokine function are described herein.

YCI polypeptides can be produced by any of a variety of methods for protein production known in the art such as production by recombinant DNA methods by inserting a DNA sequence encoding YCI, or fragments or derivatives thereof, into a recombinant expression vector and expressing the DNA sequence under conditions promoting expression. General techniques for nucleic acid manipulation are described, for example, by Sambrook et al., in "Molecular Cloning: A Laboratory Manual," 2nd Edition, Cold Spring Harbor Laboratory press, 1989; Goeddel et al., in "Gene Expression Technology: Methods in Enzymology," Academic Press, San Diego, Calif., 1990; Ausubel et al., in "Current Protocols in Molecular Biology," John Wiley & Sons, New York, N.Y., 1998; Watson et al., "Recombinant DNA," Chapter 12, 2nd edition, Scientific American Books, 1992; and other laboratory textbooks. The DNA encoding YCI is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences which control the termination of transcription and translation. The ability to replicate in a host, usually conferred by an origin of replication, and a selection gene to facilitate recognition of transformants may additionally be incorporated. The YCI nucleic acid molecule can further include nucleic acid sequences encoding additional amino acid sequences for facilitating purification. Such sequences can include a myc, FLAG, HIS, HA, GST, affinity or epitope tag. Recombinant proteins can be purified using methods well known in the art, for example in "Guide to Protein Purification" Methods in Enzymology, Volume 182, Academic Press, 1990. For proteins that have an epitope tag, numerous affinity chromatography resins are commercially available that bind specifically to tagged proteins. For native proteins that do not have a tag, traditional chromatography and/or immunoaffinity methods can be used to purify the protein. Such methods include the use of ion-exchange, hydrophobic interaction, gel-filtration, reverse phase, and affinity chromatography resins. Standard methods can be used to create an immunoaffinity chromatography resin by using antibodies specific for the recombinant protein. For example, see "Antibodies: A Laboratory Manual", Cold Spring Harbor Press, 1988.

Appropriate cloning and expression vectors for use with bacterial, fungal, yeast, insect, and mammalian cellular hosts can be found, for example, in "Cloning Vectors: A Laboratory Manual," Elsevier, New York, 1985, the relevant disclosure of which is hereby incorporated by reference.

The expression construct is introduced into the host cell using a method appropriate to the host cell, as will be apparent to one of skill in the art. The expression construct can be introduced for transient expression of the protein or stable expression by selecting cells using a selectable marker in order to generate a stable cell line that expresses the protein continuously. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells for expression of YCI polypeptides from recombinant vectors include prokaryotes, fungal, mammalian cells, or insect cells.

In one example, a method of preparing such protein molecules is embodied by (1) transferring a recombinant expression vector that includes a the YCI nucleic acid molecule set forth in SEQ ID NO: 1 into a desired host cell, (2) selecting transformed host cells from untransformed cells, (3) culturing the host cell under conditions that allow or induce the expression of the specified YCI encoded by SEQ ID NO: 1 and (4) isolation of YCI from cultured host cells using a suitable purification procedure.

Any number of standard purification techniques can be used to purify the YCI polypeptide from the cells that are secreting it. For example, if the YCI polypeptide is produced with a tag, as described above, affinity chromatography using reagents that recognize the tag (e.g., anti-myc antibodies, a histidine affinity column, and an anti-flag antibody) can be used to purify the YCI polypeptide. In one embodiment, physical and chemical characteristics of YCI as specified herein are utilized to separate said protein from other protein or non-protein molecules. Such physical and chemical characteristics include but are not limited to, density, molecular weight, isoelectric point, ligand affinity, solubility, temperature-sensitivity, etc. In another example, supernatants from systems which secrete recombinant protein into culture media can be first concentrated using a commercially available protein concentration filter, for example, an Amicon or Millipore Pellicon ultrafiltration unit, and then purified. After purification, the YCI polypeptide may be exchanged into different buffers and/or concentrated by any of a variety of methods known in the art, including, but not limited to, filtration and dialysis. The purified YCI polypeptide is preferably at least 85% pure, more preferably at least 95% pure, and most preferably at least 98% pure. Regardless of the exact numerical value of the purity, the YCI polypeptide is sufficiently pure for use as a pharmaceutical product.

YCI polypeptides, or fragments or derivatives thereof, can also be produced by chemical synthesis (e.g., by the methods described in "Solid Phase Peptide Synthesis," $2^{nd}$ ed., The Pierce Chemical Co., Rockford, Ill., 1984). Modifications to the protein, such as those described below, can also be produced by chemical synthesis.

YCI Polypeptide Modifications

The invention encompasses YCI polypeptides, or fragments or derivatives thereof, which are modified during or after synthesis or translation. Modifications may provide additional advantages such as increased affinity, decreased off-rate, solubility, stability and in vivo or in vitro circulating time of the polypeptide, or decreased immunogenicity and include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing or degradation, phosphorylation, prenylation, racemization, selenoylation, sulfation, transfer-RNA mediated addition of amino acids to proteins such as arginylation, and ubiquitination. (See, for instance, Creighton, "Proteins: Structures and Molecular Properties," 2d Ed., W.H. Freeman and Co., N.Y., 1992; "Postranslational Covalent Modification of Proteins," Johnson, ed., Academic Press, New York, 1983; Seifter et al., *Meth. Enzymol.*, 182:626-646, 1990; Rattan et al., *Ann. NY Acad. Sci.*, 663:48-62, 1992). Additionally, the YCI polypeptide may contain one or more non-classical amino acids. Non-classical amino acids include, but are not limited to, to the D-isomers of the common amino acids, 2,4-diaminobutyric acid, α-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression.

As described above, the invention also includes chemically modified derivatives of YCI, which may provide additional advantages such as increased solubility, stability, and circulating time of the polypeptide, or decreased immunogenicity (see U.S. Pat. No. 4,179,337). The chemical moieties for derivitization may be selected from water soluble polymers such as, for example, polyethylene glycol, ethylene glycol/propylene glycol copolymers, carboxymethylcellulose, dextran, polyvinyl alcohol and the like. The YCI polypeptide may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72, (1996); Vorobjev et al., *Nucleosides Nucleotides* 18:2745-2750, (1999); and Caliceti et al., *Bioconjug. Chem.* 10:638-646, (1999), the disclosures of each of which are incorporated by reference.

The polyethylene glycol molecules (or other chemical moieties) should be attached to the YCI polypeptide with consideration of effects on functional or antigenic domains of the protein. There are a number of attachment is methods available to those skilled in the art, e.g., EP 0 401 384, herein incorporated by reference (coupling PEG to G-CSF), see also Malik et al., *Exp. Hematol.* 20:1028-1035, (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. The number of polyethylene glycol moieties attached to each polypeptide of the invention (i.e., the degree of substitution) may also vary. For example, the pegylated YCI may be linked, on average, to 1, 2, 3, 4, 5, 6, 7, 8, 9, 10, 12, 15, 17, 20, or more polyethylene glycol molecules. Similarly, the average degree of substitution may range within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per polypeptide molecule. Methods for determining the degree of substitution are discussed, for example, in Delgado et al., *Crit. Rev. Thera. Drug Carrier Sys.*, 9:249-304, 1992.

The YCI polypeptides may also be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of a YCI target. The detectable substance may be coupled or conjugated either directly to the polypeptides of the invention or indirectly, through an intermediate (such as, for example, a linker known in the art) using techniques known in the art. Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichloro-triazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R $^{188}$Re, $^{142}$Pr, $^{105}$Rh, $^{97}$Ru, $^{68}$Ge $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin. The detectable substance may be coupled or conjugated either directly to the polypeptide or indirectly, through an intermediate (such as, for example, a linker known in the art) using techniques known in the art.

The YCI polypeptide can also be modified by conjugation to another protein or therapeutic compound. Such conjugation can be used, for example, to enhance the stability or solubility of the protein, to reduce the antigenicity, or to enhance the therapeutic effects of the protein. This may be accomplished by covalent attachment of conjugating molecules to any residue of the specified YCI polypeptide, or related truncations, analogs and homologs thereof.

YCI Nucleic Acid Molecules

YCI nucleic acids, or fragments or derivatives thereof, are also useful in the methods of the invention. The nucleic acids encoding the desired YCI may be obtained using routine procedures in the art, e.g. recombinant DNA or PCR amplification. For any of the nucleic acid applications described herein, standard methods for administering nucleic acids can be used. Examples are described in U.S. Patent Application Publication No. 20060067937 and PCT Publication No. WO 06/034507.

The scope of this invention includes variations of the YCI nucleic acid sequences defined as follows:
(1) fragments or derivatives of the YCI nucleic acid sequences;
(2) nucleic acid sequences differing from SEQ ID NO: 1 by substitution of a T with a U;
(3) nucleic acid sequences complimentary to either the full length of SEQ ID NO: 1, or complimentary to nucleic acid fragments derived thereof;
(4) nucleic acid sequences that hybridize with the nucleic acid sequences represented within SEQ ID NO: 1;
(5) nucleic acid sequences differing from the full length of SEQ ID NO: 1 due to the degeneracy of the genetic code.

In one embodiment, this invention contemplates a purified or isolated double stranded nucleic acid molecule formed through hydrogen bonding of the nucleic acid molecules specified in SEQ ID NO:1, or fragments or derivatives thereof, to a complimentary nucleic acid sequence.

The nucleic acid molecules specified herein as SEQ ID NO:1 may also be inserted into an expression vector that contains necessary elements upstream and downstream of the inserted nucleic acid for the transcription and translation of the inserted sequence within prokaryotic and eukaryotic cells. The invention embodies expression vectors which comprise a nucleic acid molecule specified in SEQ ID NO:1, or related fragments or derivatives thereof, with one or more transcription and translation elements operatively linked to the nucleic acid molecule. Possible expression vectors include, but are not limited to, cosmids, plasmids and modified viral vectors (replication-defective retroviruses, adenoviruses and adeno-associated viruses).

Recombinant expression vectors may be used to prepare transformed cell lines that include YCI nucleic acid molecules (e.g., SEQ ID NO:1 or sequences encoding a YCI polypeptide), or fragments or derivatives thereof. This invention provides cell lines, including eukaryotic and prokaryotic cell types, containing a recombinant YCI nucleic acid molecule (e.g., SEQ ID NO:1 or nucleic acid sequences encoding a YCI polypeptide), or related fragments or derivatives thereof.

This invention also contemplates transgenic non-human animals whose germ cells and somatic cells contain a recombinant molecule comprising a nucleic acid molecule specified in SEQ ID NO: 1, or a related fragment or derivative thereof. Such sequences may be expressed in non-human species including but not limited to zebrafish, xenopus, drosophila, mice, rats, rabbits, sheep, pigs, and chickens.

YCI Antibodies

This invention also contemplates antibodies or antibody-derived fragments that specifically bind a YCI polypeptide (e.g., SEQ ID NO:2) or any fragment thereof. Therefore, this invention also provides a method of generating antibodies within mammalian species through injection of the YCI polypeptide (e.g., SEQ ID NO:2) or fragments or derivatives of the amino acid sequence thereof into a mammalian organism.

Furthermore, antibodies or antibody fragments that specifically bind YCI polypeptides, or fragments or derivatives thereof, may be labeled with detectable substances, such as fluorochromes or peroxidases, that permit detection of the YCI, or related sequences specified within SEQ ID NO:2, within tissues and cells. The invention also covers use of such antibodies to purify YCI or its related fragments or derivatives thereof from cells and tissues.

YCI Nucleic Acid Probes

This invention also provides a method for the design and construction of nucleotide probes unique to YCI nucleic acid molecules or fragments or derivatives thereof. Such nucleotide probes may also be labeled with detectable substances that permit detection of YCI nucleic acid sequences within tissues and cells. In addition, nucleotide probes may also be utilized as a diagnostic tool to assess the upregulation of YCI expression within cells. Labeled nucleotide probes may alternatively be used to identify YCI related nucleic acid molecules from a heterogeneous population of deoxyribonucleic acids and/or ribonucleic acids (e.g., a cDNA library, a genomic DNA library or a genomic RNA library).

This invention also embodies the use of the polymerase chain reaction or related polymerase reactions to amplify or generate nucleic acids encoding YCI, including fragments or derivatives thereof. In one embodiment, synthetic oligonucleotide primers generated from segments of the nucleotide sequence disclosed in SEQ ID NO: 1 can be utilized to amplify YCI-encoding sequence(s) from genomic DNA, cDNA libraries, RNA molecules or other nucleic acid mixtures.

Uses of YCI Nucleic Acids and Polypeptides of the Invention

This invention also provides a method of modulating YCI expression within cells, tissues, organs and organisms. The introduction of nucleic acid molecules into cells and tissues may be utilized to amplify the transcription and translation of YCI nucleic acids, or fragments or derivatives thereof. Alternatively, YCI expression may be downregulated by the introduction of complimentary nucleic acid sequences (e.g., antisense or double stranded RNA) that block transcription and translation of YCI-encoding nucleic acids or fragments or derivatives thereof.

In preferred embodiments of the invention, the YCI polypeptide, or fragments or derivatives thereof, can bind one or more types of chemokines derived from or present within mammalian organisms. Therefore, the present invention includes methods of modulating chemokine or cytokine function by contacting a cell with a YCI polypeptide or a YCI nucleic acid molecule. The invention also includes methods of administering YCI polypeptides or nucleic acid molecules in vivo to bind one or more chemokine proteins within mammalian organisms. Furthermore, YCI may be administered or expressed within specific mammalian tissues to bind chemokines present within the tissue. It is envisioned herein that the binding between YCI and the chemokine will reduce, inhibit and/or otherwise diminish (e.g., by at least 10%, 20%, 30%, 40%, 50%, 60%, 70%, 80%, 90% or more) the biological activity of the chemokine within mammalian organisms. In one embodiment, the YCI polypeptide will bind to the chemokine in the region of the chemokine responsible for interaction with its cognate receptor, thereby preventing the covalent or non-covalent interaction between said chemokine and its corresponding chemokine receptor.

YCI polypeptides of the invention may also bind mammalian cytokines, other than those defined herein as chemokines. Therefore, the present invention includes methods of administering YCI polypeptides or nucleic acid encoding a YCI polypeptide, or fragments or derivatives thereof, to mammalian tissues or cells or to the mammal itself to bind one or more cytokine proteins within mammalian organisms. Alternatively, YCI may be administered or expressed within specific mammalian tissues to bind cytokines, other than those herein defined as chemokines, within the tissue. It is envisioned herein that the binding between YCI and said cytokine shall reduce, inhibit and/or otherwise diminish (e.g., by at least 10%, 20%, 30%, 40%, 50%, 60%, 70%, 80%, 90%, or more) the biological activity of the cytokine, for example, IL-18, within the mammalian tissue, cell, or organism (e.g., binding to IL-12 or induction of IFN-γ). In one embodiment, the binding between YCI and one or more cytokine(s) shall occur in the region of the cytokine molecule responsible for interaction with a corresponding receptor thereof, hence preventing the covalent or non-covalent interaction between said cytokine and its corresponding cytokine receptor. In another embodiment, the binding between the YCI and the one or more cytokine will result in a sequestering of the cytokine and an inhibition of the biological activity of the cytokine.

In another preferred embodiment, the YCI polypeptide may bind mammalian chemokine or cytokine receptors, as defined above. Such binding between YCI and one or more chemokine or cytokine receptors may occur at the extracellular domain of the receptor. Furthermore, it is envisioned herein that such binding between YCI and one or more of the chemokine or cytokine receptors may disrupt normal signaling known within the art to occur upon binding of the cytokine ligand. As such, YCI polypeptides of the invention may be administered in vivo to bind one or more chemokine or cytokine receptors and modulate, preferably reduce, inhibit and/or other diminish (by at least 10%, 20%, 30%, 40%, 50%, 60%, 70%, 80%, 90% or more) the signaling functions mediated by such chemokine or cytokine receptors.

This invention further provides a method for the identification of substances capable of binding a YCI polypeptide, or fragments or derivatives thereof, from viral, bacterial or mammalian sources. In one embodiment, the YCI polypeptide is present in proximity to other proteins derived from mammalian sources, including the appropriate conditions necessary for binding to occur, while binding is detected using YCI-specific labeled antibodies. In another embodiment, a yeast two hybrid assay system is utilized as a method for the identification of proteins interacting with YCI, or fragments or derivatives thereof. In another embodiment, interactions between YCI and other proteins, including but not restricted to immune-related proteins, are detected through cross-linking agents, as are known within the art, that mediate covalent bonds between YCI and other proteins that demonstrate significant affinity thereto.

This invention further provides a method of identifying agents that affect the transcription and or translation of YCI nucleic acid molecules within cells expressing the nucleic acid molecule, including fragments, or derivatives thereof. In one embodiment, the pattern and level of YCI encoding RNA and full-length protein is assayed upon treatment of YCI expressing cells under assay conditions including, but not limited to, the treatment of YCI expressing cells with growth factors, hormones, cytokines, phorbol esters, hemagglutinins, antibodies and antibody fragments.

The invention herein also provides a method of identifying agents that modulate post-translational modification of YCI, including fragments and derivatives thereof. Such modifications may play a role in YCI protein functions, cytokine protein functions, chemokine protein functions, chemokine receptor functions and other functions or dysfunctions derived thereof. Examples of such modifications include, but are not limited to, protein folding, disulfide linkage, glycosylation, myristylation, palmitoylation, tyrosine phosphorylation, serine phosphorylation, threonine phosphorylation, ubiquitination, and proteolytic degradation.

This invention also provides methods for the generation of experimental models for the study of YCI-encoding nucleic acid and protein functions under in vivo or in vitro conditions. Cells, tissues and non-human animals that express, overexpress, or underexpress YCI polypeptides or nucleic acid molecules, or fragments or derivatives thereof, can be established according to the embodiments of the invention herein. In particular, the generation of transgenic non-human animals may be accomplished via nuclear oocyte microinjection of YCI nucleic acids will provide novel models for the determination of YCI structure and function. This invention also permits the use of YCI nucleic acids to develop cell lines to study the effect of YCI expression, over-expression or underexpression in various developmental systems, including, but not limited to, hematopoesis, neurogenesis, mammary development and lung epithelial development, cell homeostasis, cell signaling, cell death, differentiation and neuronal development.

Therapeutic Uses

The invention also includes therapeutic uses of the YCI polypeptide or nucleic acids of the invention for treating or preventing an immunoinflammatory disorder. In one example, the YCI polypeptide or nucleic acid molecule of the invention is utilized to reduce, treat, prevent, or otherwise lower (e.g., by at least 10%, 20%, 30%, 40%, 50%, 60%, 70%, 80%, 90% or more) disease conditions or symptoms associated or mediated by inflammation (e.g., an immunoinflammatory disorder) in a mammalian subject, preferably a human. In one preferred embodiment, nucleic acid molecules encoding YCI polypeptides are introduced into a mammalian animal through methods and procedures well known within the art. In such situations, it is envisioned that such nucleic acids shall be introduced into cells and tissues that shall mediate replication, transcription and/or translation of the nucleic acids. In another preferred embodiment, nucleic acid molecules encoding YCI polypeptides are introduced into a specific tissue or cell type of a mammalian animal for the treatment, prevention and/or reduction of disease conditions associated or mediated by inflammation (e.g., an immunoinflammatory disorder). In yet another preferred embodiment, YCI nucleic acids are introduced into cells and tissues in in vitro or ex vivo conditions, that will mediate replication, transcription and/or transplantation of said nucleic acids, prior to the transplantation of such YCI-expressing cells and tissues into a mammalian organism for the purpose of reducing, treating, preventing and otherwise lowering disease conditions associated or mediated by inflammation (e.g., an immunoinflammatory disorder).

The invention disclosed herein further contemplates the therapeutic use of a YCI polypeptide, or fragments, derivatives, or modifications thereof, for the purpose of treating, preventing, reducing or otherwise lowering (e.g., by at least 10%, 20%, 30%, 40%, 50%, 60%, 70%, 80%, 90% or more) disease conditions associated or mediated by inflammation (e.g., an immunoinflammatory disorder). In one preferred embodiment, YCI polypeptides, or fragments, derivatives, or modifications thereof, are specifically introduced into a subject, preferably a mammal or, more preferably a human, in vivo within a specific tissue type that is known within the art to be the site or location of a disease condition associated or mediated by inflammation. In another embodiment, the YCI disclosed herein, or fragments, derivatives, or modifications thereof, are introduced into cells and/or a tissue while under in vitro or ex vivo conditions, prior to the transplantation of the cells and/or a tissue into a mammalian organism for the purpose of treating, preventing, reducing or otherwise lowering disease conditions or symptoms associated or mediated by inflammation.

Further envisioned within the scope of this invention is the usage of YCI nucleic acids or proteins, or fragments or derivatives thereof, for the treatment of all human diseases and/or conditions that are mediated or associated with the onset of inflammation, as well as human diseases and/or conditions that are mediated or associated with autoimmunity. Such diseases and/or conditions are referred to herein as immunoinflammatory disorders and include but are not restricted to inflammation, autoimmune disease and immune-mediated disorders, which include but are not restricted to acute inflammation, rheumatoid arthritis, transplant rejection, transplant vasculopathy, asthma, allergic inflammation, restenosis, arterial restenosis, by-pass graft occlusion, Guacher's disease, inflammatory bowel disease, uveitis, multiple sclerosis, psoriasis, wound healing, lupus erythematosus, allergic rhinitis, atopic dermatitis, food allergies, type 1 insulin-dependent diabetes mellitus, deramatitis, meningitis, thrombotic thrombocytopenic purpura, Sjogren's syndrome, encephalitis, leukocyte adhesion deficiency, rheumatic fever, Reiter's syndrome, psoriatic arthritic, osteoarthritis, ocular inflammatory disorders, progressive systemic sclerosis, primary biliary cirrhosis, pemphigus, pemphigoid, necrotizing vasculitis, mayasthenia gravis, lupus erythematosus, polymyositis, sarcoidosis, granulomatorsis, vasculitis, pernicious anemia, CNS inflammatory disorder, antigen-antibody complex mediated diseases, autoimmune hemolytic anemia, Hashimoto's thyroiditis, Graves disease, habitual spontaneous abortions, Reynard's syndrome, glomerulonephritis, dermatomyositis, chromic active hepatitis, celiac disease, autoimmune complications of AIDS, atrophic gastritis, ankylosing spondylitis, Addison's disease, psoriasis, penphigus vularis, Behcet's syndrome, acute respiratory distress syndrome (ARDS), ischemic heart disease, atherosclerosis, post-dialysis syndrome, leukemia, acquired immune deficiency syndrome, septic shock, lipid histiocytosis, and cancer.

Also included in the invention are pharmaceutical compositions that include a YCI polypeptide or nucleic acid molecule, or fragments or derivatives thereof, and a pharmaceutically acceptable carrier. This invention also contemplates that reagents suitable for the therapies and diagnostics outlined herein may be administered using pharmaceutically acceptable vehicles. Such vehicles include, but are not limited to, expression vectors, microinjection, liposome delivery, subcutaneous injection, intravenous injection, oral administration, inhalation, transdermal application or rectal administration. Such vehicles and related therapeutic regima may be optimized for according to factors such as disease stage, age, sex and weight of the individual. In one embodiment, reagents suitable for the therapies and diagnostics outlined herein may be packaged into convenient kits providing the necessary materials packaged into suitable containers. Such kits may include suitable supports useful and assisting in performing the therapeutic and diagnostic strategies outlined herein.

In various embodiments YCI nucleic acids or polypeptides, or fragments or derivatives thereof, can be provided in conjunction (e.g., before, during, or after) with additional anti-immunoinflammatory therapies to treat or prevent the immunoinflammatory disorder. Such therapies are known in the art and examples are described in U.S. Patent Application Publication No. 20050119160, herein incorporated by reference.

Therapeutic Formulations

The YCI polypeptides and nucleic acid molecules of the present invention can be formulated and administered in a variety of ways, e.g., those routes known for specific indications, including, but not limited to, topically, orally, subcutaneously, intravenously, intracerebrally, intranasally, transdermally, intraperitoneally, intramuscularly, intrapulmonary, vaginally, rectally, intraarterially, intralesionally, parenterally, intraventricularly in the brain, or intraocularly. The YCI polypeptides and nucleic acid molecules can be in the form of a pill, tablet, capsule, liquid, or sustained release tablet for oral administration; or a liquid for intravenous, subcutaneous or administration; or a polymer or other sustained release vehicle. In one example, the YCI polypeptides or nucleic acid molecules are administered continuously by infusion, using a constant- or programmable-flow implantable pump, or by periodic injections. Administration can be continuous or periodic. Semipermeable, implantable membrane devices are also useful as a means for delivering YCI polypeptides or nucleic acids in certain circumstances. In another embodiment, the YCI polypeptide or nucleic acid molecule is administered locally, e.g., by direct injections, when the disorder or location of the inflammation permits, and the injections can be repeated periodically. Such local administration is particularly useful in the prevention and treatment of local immunoinflanunation.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.), in the form of lyophilized formulations or aqueous solutions. Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant. Preferred surfactants are non-ionic detergents. Preferred surfactants include Tween 20 and pluronic acid (F68). Suitable surfactant concentrations are 0.005 to 0.02%.

The dosage required depends on the choice of the route of administration; the nature of the formulation; the nature of the subject's illness; the subject's size, weight, surface area, age, and sex; other drugs being administered; and the judgment of the attending physician.

Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 6-, 8-, 10-, 20-, 50-, 100-, 150-, or more). Encapsulation of the polypeptide in a suitable delivery vehicle (e.g., polymeric microparticles or implantable devices) may increase the efficiency of delivery, particularly for oral delivery.

Alternatively, a YCI polypeptide or YCI nucleic acid molecule can be delivered to the appropriate cells in the subject. Expression of the coding sequence can be directed to any cell in the body of the subject. In certain embodiments, expression of the YCI nucleic acid coding sequence can be directed to the site of inflammation. This can be achieved by, for example, the use of polymeric, biodegradable microparticle or microcapsule delivery devices known in the art.

The YCI nucleic acid can be introduced into the cells by any means appropriate for the vector employed. Many such methods are well known in the art (Sambrook et al., supra, and Watson et al., Recombinant DNA, Chapter 12, 2d edition, Scientific American Books, 1992). Examples of methods of gene delivery include liposome mediated transfection, electroporation, calcium phosphate/DEAE dextran methods, gene gun, and microinjection.

In gene therapy applications, genes are introduced into cells in order to achieve in vivo synthesis of a therapeutically effective genetic product. "Gene therapy" includes both conventional gene therapy where a lasting effect is achieved by a single treatment, and the administration of gene therapeutic agents, which involves the one time or repeated administration of a therapeutically effective DNA or mRNA. Standard gene therapy methods typically allow for transient protein expression at the target site ranging from several hours to several weeks. Re-application of the nucleic acid can be utilized as needed to provide additional periods of expression of YCI.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al., *J. Mol. Med.* 73:479,1995). Alternatively, tissue specific targeting can be achieved by the use of tissue-specific transcriptional regulatory elements which are known in the art. Delivery of "naked DNA" (i.e., without a delivery vehicle) to an intramuscular, intradermal, or subcutaneous site is another means to achieve in vivo expression.

Gene delivery using viral vectors such as adenoviral, retroviral, lentiviral, or adeno-associated viral vectors can also be used. Numerous vectors useful for this purpose are generally known and have been described (Miller, *Human Gene Therapy* 15:14, 1990; Friedman, *Science* 244:1275-1281, 1989; Eglitis and Anderson, *BioTechniques* 6:608-614, 1988; Tolstoshev and Anderson, *Current Opinion in Biotechnology* 1:55-61, 1990; Sharp, *The Lancet* 337:1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; Miller and Rosman, *Biotechniques* 7:980-990, 1989; Rosenberg et al., *N. Engl. J. Med* 323:370, 1990; Groves et al., *Nature,* 362:453-457, 1993; Horrelou et al., *Neuron,* 5:393-402, 1990; Jiao et al., *Nature* 362:450-453, 1993; Davidson et al., *Nature Genetics* 3:2219-2223, 1993; Rubinson et al., *Nature Genetics* 33, 401-406, 2003; and U.S. Pat. Nos. 6,180,613; 6,410,010; and 5,399,346 all hereby incorporated by reference). These vectors include adenoviral vectors and adeno-associated virus-derived vectors, retroviral vectors (e.g., Moloney Murine Leukemia virus based vectors, Spleen Necrosis Virus based vectors, Friend Murine Leukemia based vectors, lentivirus based vectors (Lois et al., *Science,* 295:868-872, 2002; Rubinson et al., supra), papova virus based vectors (e.g., SV40 viral vectors), Herpes-Virus based vectors, viral vectors that contain or display the Vesicular Stomatitis Virus G-glycoprotein Spike, Semliki-Forest virus based vectors, Hepadnavirus based vectors, and Baculovirus based vectors.

In the relevant polynucleotides (e.g., expression vectors), the nucleic acid sequence encoding the YCI polypeptide (including an initiator methionine and optionally a targeting sequence) is operatively linked to a promoter or enhancer-promoter combination. Short amino acid sequences can act as signals to direct proteins to specific intracellular compartments. Such signal sequences are described in detail in U.S. Pat. No. 5,827,516, incorporated herein by reference in its entirety.

The dosage and the timing of administering the compound depends on various clinical factors including the overall health of the subject and the severity of the symptoms. In general, once an immunoinflammatory disorder is detected, any of the methods for administering the YCI polypeptides or nucleic acids described herein can be used to treat or prevent further progression of the condition. For example, continuous systemic infusion or periodic injection to the site of the inflammation of the YCI polypeptide, or fragments or derivatives thereof, can be used to treat or prevent the disorder. Treatment can be continued for a period of time ranging from 1 day through the lifetime of the subject. For treating subjects, between approximately 0.001 mg/kg to 500 mg/kg body weight of the YCI polypeptide or nucleic acid molecule can be administered. A more preferable range is 0.01 mg/kg to 50 mg/kg body weight with the most preferable range being from 0.1 mg/kg to 25 mg/kg body weight. Depending upon the half-life of the YCI polypeptide in the particular subject, the compound can be administered between several times per day to once a week. The methods of the present invention provide for single as well as multiple administrations, given either simultaneously or over an extended period of time.

Where sustained release administration of a YCI polypeptide is desired in a formulation with release characteristics suitable for the treatment of any disease or disorder requiring administration of the YCI polypeptide, microencapsulation of the YCI polypeptide is contemplated. Micro encapsulation of recombinant proteins for sustained release has been successfully performed with human growth hormone (rhGH), interferon-(rhIFN-), interleukin-2, and MN rgp120. Johnson et al., Nat. Med., 2:795-799, 1996; Yasuda, Biomed. Ther., 27:1221-1223, 1993; Hora et al., *Bio/Technology*, 8:755-758, 1990; Cleland, "Design and Production of Single Immunization Vaccines Using Polylactide Polyglycolide Microsphere Systems," in "Vaccine Design: The Subunit and Adjuvant Approach," Powell and Newman, eds., Plenum Press: New York, pp. 439-462, 1995; WO 97/03692; WO 96/40072; WO 96/07399; and U.S. Pat. No. 5,654,010.

The sustained-release formulations may include those developed using ply-lactic-coglycolic acid (PLGA) polymer. The degradation products of PLGA, lactic and glycolic acids, can be cleared quickly within the human body. Moreover, the degradability of this polymer can be adjusted from months to years depending on its molecular weight and composition. See Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990.

Additional formulations and modes of administration for the treatment or prevention of immunoinflammatory disorders are known in the art and described, for example, in U.S. Patent Application Publication No. 20050119160, herein incorporated by reference.

The YCI polypeptide or nucleic acid molecule can be packaged alone or in combination with other therapeutic compounds as a kit. Non-limiting examples include kits that contain, e.g., two pills, a pill, and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

EXAMPLES

The following examples are intended to illustrate the invention. They are not meant to limit the invention in any way.

Example 1

Purification of Two Forms of YCI

The IL-18 bp from YMTV, also known as YCI, was discovered during genomic sequencing of the virus genome, and was identified because of its homology with other known IL-18 binding proteins. The gene encoding the IL-18 bp from YMTV was cloned and expressed in a baculovirus expression system. Two forms of the product have been isolated and tested. In one form, the YMTV IL-18 bp is expressed with a C-terminal myc/his tag (hereinafter referred to as "tagged YCI"), to facilitate purification. The his-tagged version of the YCI was purified using immobilized metal affinity chromatography methods, which takes advantage of the well-described affinity that his-tags have for metal ions. In a second form, the YMTV IL-18 bp was not tagged (hereinafter referred to as "untagged YCI"), and the protein was purified using a combination of ion-exchange, hydrophobic interaction, and gel-filtration chromatography. Both forms of the protein are expressed as secreted proteins from cells infected with the recombinant baculovirus.

Example 2

Purified YCI Binds Both Human and Murine IL-18 at Nanomolar Concentrations

Using the purified tagged and untagged YCI proteins, we have studied the activity of the proteins with respect to their ability to bind to cytokines. We immobilized the purified untagged YCI protein on a Biacore CM5 chip by amine coupling according to the manufacturer's instructions. Different cytokines were passed over the immobilized protein to measure the interaction of the cytokine with the protein. Sensograms showing the results of these experiments are shown in FIGS. 2A-2B. Injection of human IL-18 (FIG. 2A) and mouse IL-18 (FIG. 2B) was started at 0 seconds and was stopped at 60 seconds. Affinity constants are shown in the top right of each panel and concentrations of the cytokine are labeled at the end of each sensogram. These results demonstrate that purified untagged YCI interacted with human and mouse IL-18 at nanomolar concentrations.

The binding properties of tagged and untagged YCI are summarized in Table 1, below.

TABLE 1

| Cytokine binding properties of tagged and untagged YCI. | | |
|---|---|---|
| | Untagged YCI | Tagged YCI |
| IL-18 assay | + | + |
| Human/mouse IL-18 Biacore | + | + |
| Human IL-18 immunoprecipitation | + | + |

Example 3

YCI Inhibits IFN-γ Production in a Dose-Dependent Manner

We have used an in vitro system to test the ability of YCI to inhibit IFN-γ production. For these experiments we used KG-1 cells. The expression of IFN-γ can be induced in KG-1 cells by incubating the cells with a mixture of human TNF-alpha and IL-18 (Konishi et al, 1997 *J. Immun. Method* 209: 187-191).

Figure 3:
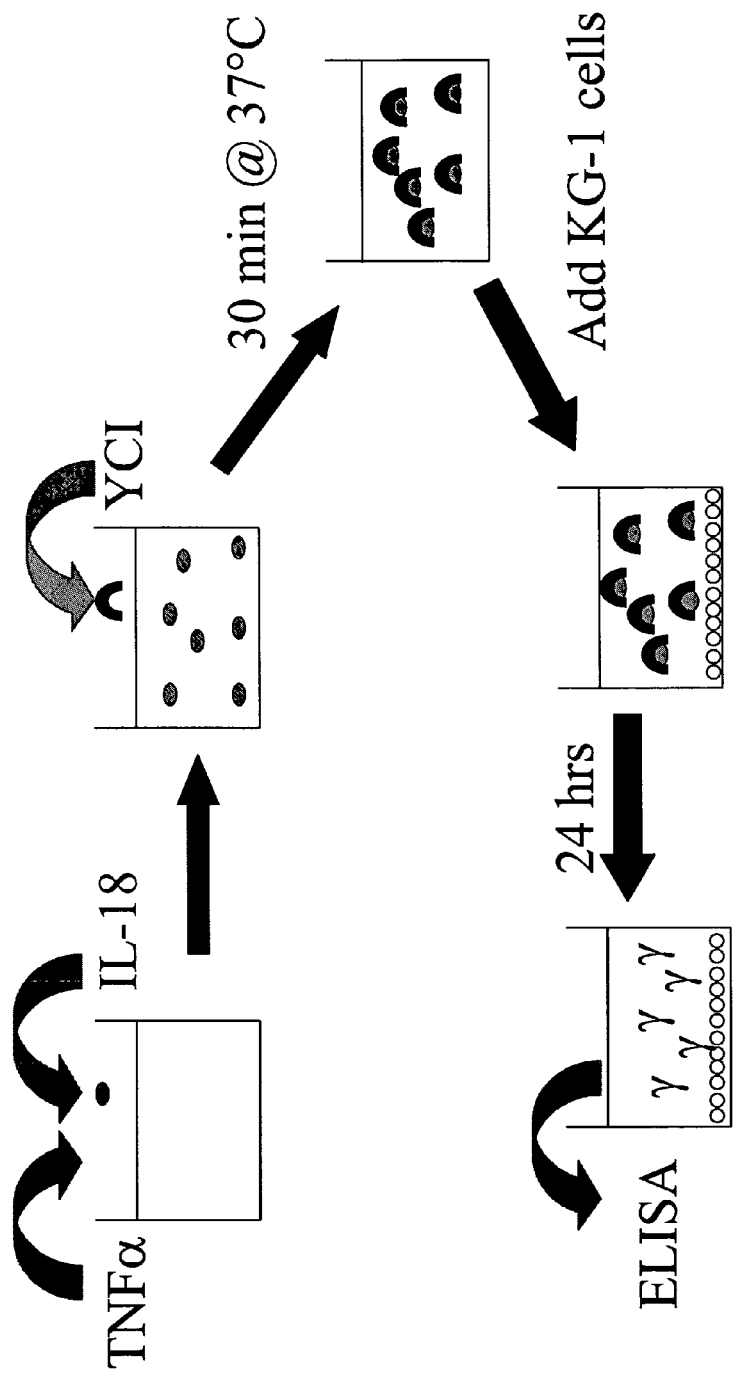
FIG. 3 is a schematic depicting the assay for IL-18 function used in FIG. 4.
Figure 4:
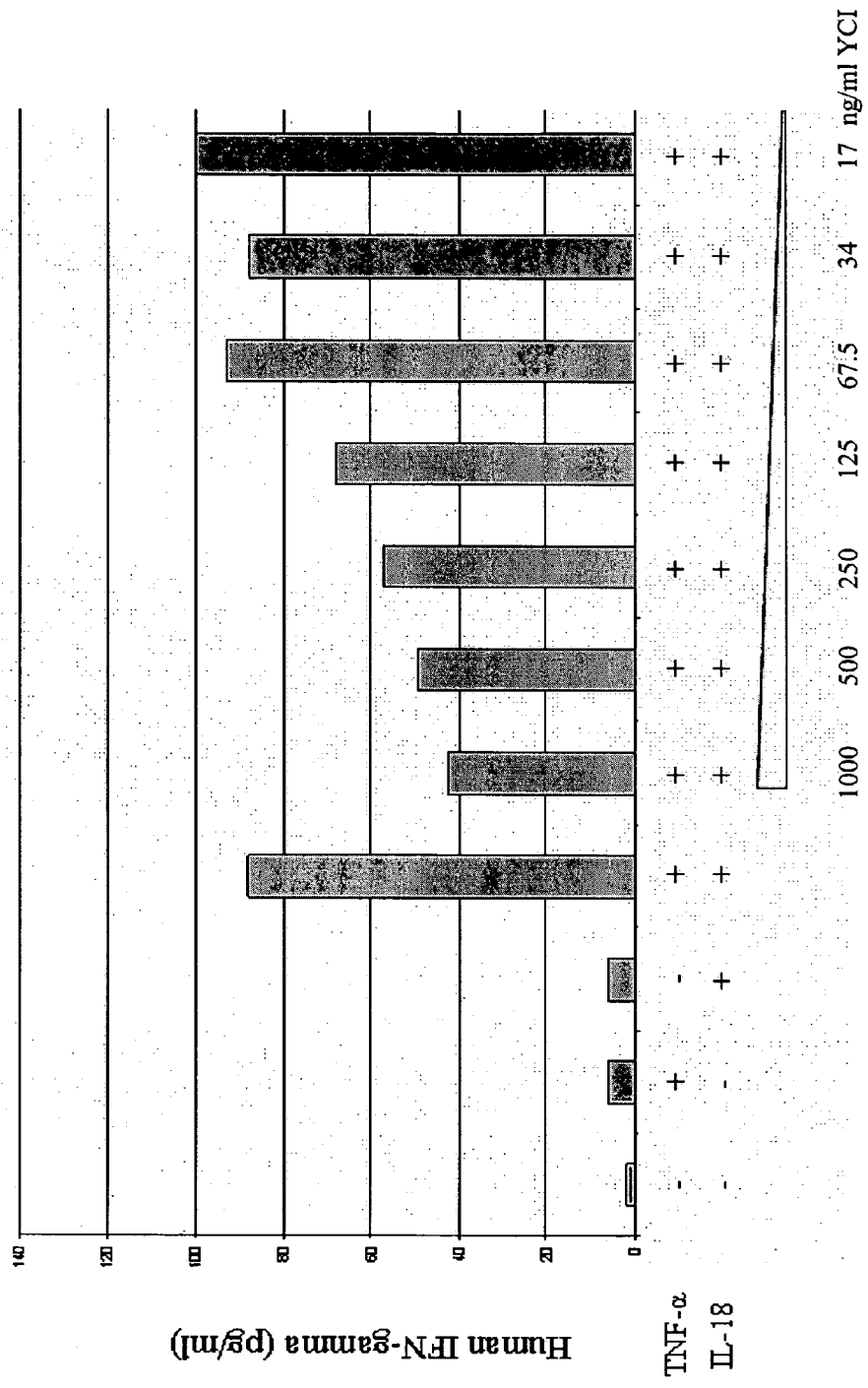
FIG. 4 is a graph showing the dose-dependent inhibition of IFN-γ production by YCI in KG-1 cells. The wedge indicates amounts of YCI added.

In this assay, summarized in FIG. 3, hIL-18 (10 ng/ml), TNF-α (10 ng/ml), and various concentrations of purified YCI were incubated in a 96 well plate at 37° C. for 30 minutes in complete cell culture media (RPMI). Human KG-1 cells were then added at a final concentration of $2 \times 10^6$ cells per ml, and incubated for 24 hours. After 24 hours, the cultures were frozen and thawed three times, the cells removed by centrifugation, and the level of human IFN-γ in the clarified media was determined by using a commercially available ELISA (EBioscience). As shown in FIG. 4, YCI showed a dose dependent inhibition of IFN-gamma production in KG-1 cells.

Example 4

Figure 5:
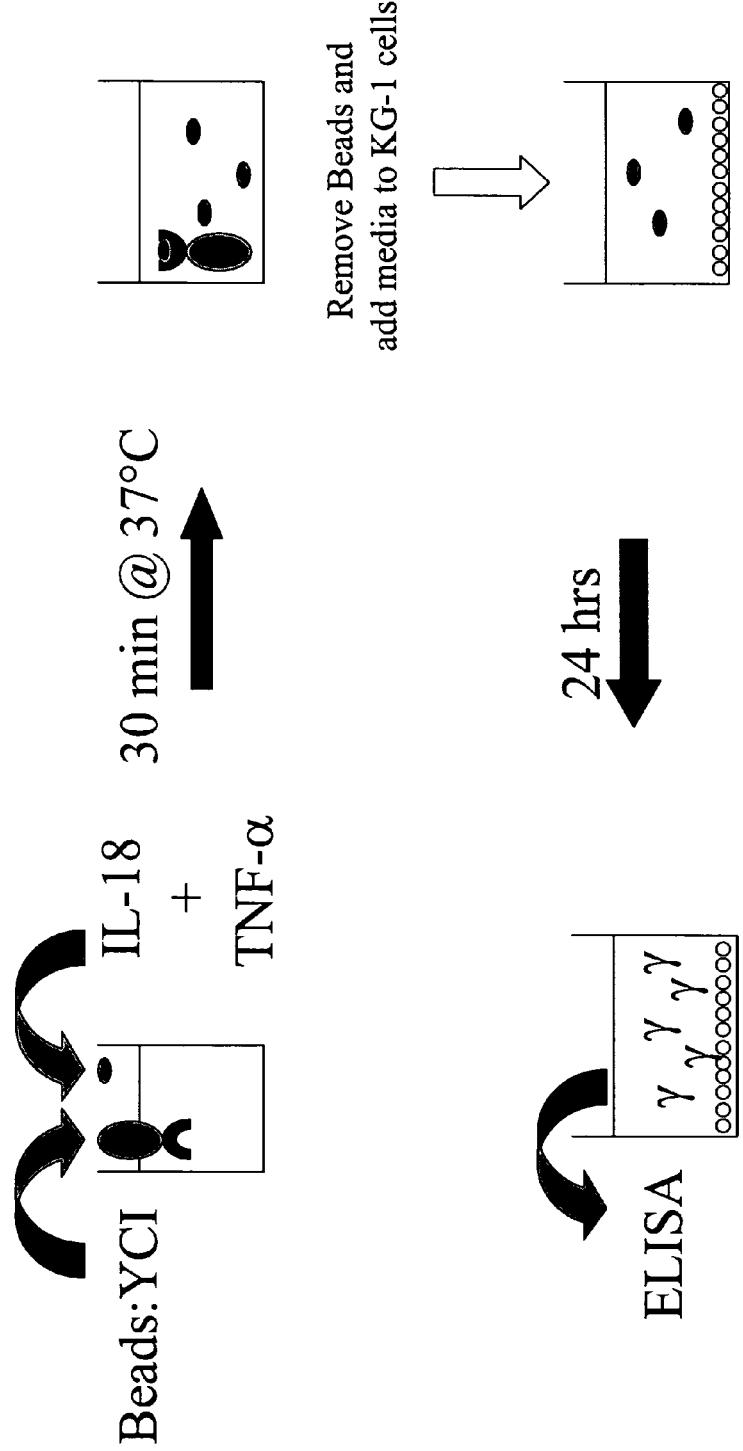
FIG. 5 is a schematic depicting the assay for IL-18 sequestration used in FIG. 6.

YCI can Sequester hIL-18 in a Dose Dependent Manner and Reduce the Induction of IFN-Induced IFN-γ in KG-1 Cells In order to determine if the effect of YCI on IFN-γ involved IL-18 sequestration, we performed an assay for IL-18 sequestration (shown in FIG. 5). This assay uses the purified tagged YCI protein described in Example 1 linked to Sepharose beads through an antibody, to deplete media samples of added IL-18. When samples are depleted of IL-18, then INF-gamma is not induced in the KG-1 cell-based assay (Konishi et al, 1997 *J. Immun. Method.* 209: 187-191). Protein A/G Sepharose was incubated with an anti-6xHis monoclonal antibody (Qiagen) for 1 hour and washed with complete RPMI. The anti-His mAb linked Sepharose was incubated with either conditioned media from cells infected with baculovirus expressing the 6xHis-tagged YCI, or with conditioned media from cells infected with control baculovirus. After 1 hour, the Sepharose beads were washed in RPMI media. A sample of human IL-18 (100 ng/ml) in RPMI was mixed with varying amounts of the Sepharose beads bound with YCI for 30 minutes. The media was then recovered and supplemented with a 1 in 10 dilution of HK-1 cells ($2\times10^6$ cells/ml) in complete RPMI with 10 ng/ml of TNF-alpha. After 24 hrs, the cultures were frozen and thawed three times, the cells removed by centrifugation, and the level of human IFN-γ in the clarified media was determined by ELISA (EBioscience).

Figure 6:
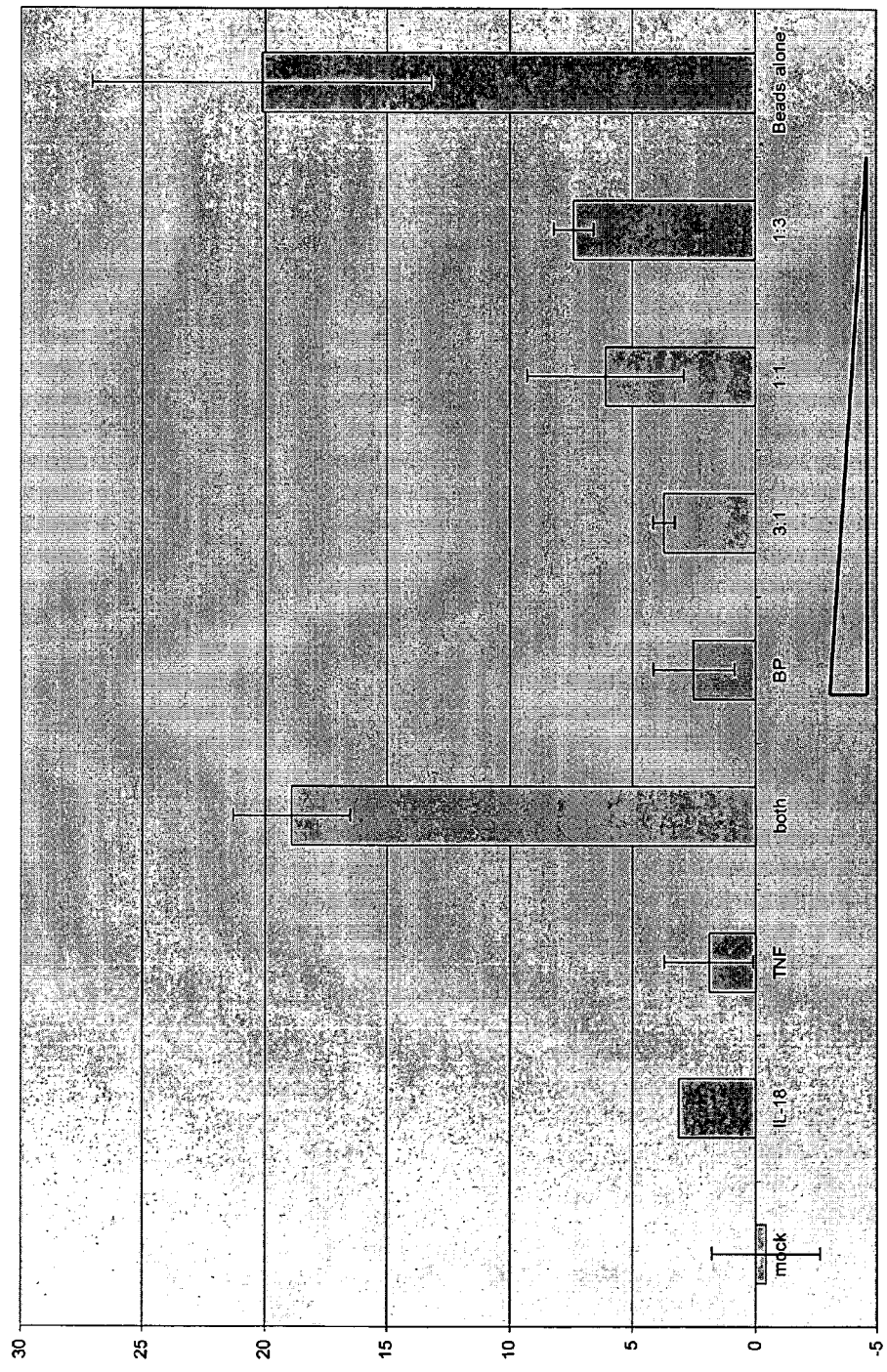
FIG. 6 is a graph showing the ability of YCI to sequester human IL-18 in a dose-dependent manner and reduce the induction of IFN-γ in KG-1 cells. The wedge indicates amounts of YCI added.

The results of this assay are shown in FIG. 6. The wedge denotes the amount of YCI beads in the mixture. The sample labeled "Beads Alone" used the antibody Sepharose beads that were mixed with media from the control baculovirus sample. These results show that the YCI was able to sequester human IL-18 in a dose dependent manner, and reduce the induction of IFN-gamma in KG-1 cells.

OTHER EMBODIMENTS

Other objects, features and advantages of the present invention that become clear as a result of the methods provided herein and depicted in the enclosed drawings are included in this invention. It should be understood that examples and preferred embodiments of the invention herein are given by way of illustration and various alterations and modifications within the spirit of the invention are included as part of the invention herein. Those skilled in the art will recognize alterations and modifications of the invention herein that must however be respected as a part of the present invention.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority, including U.S. Ser. No. 10/455,000, International Application No. PCT/CA01/01734, and U.S. Ser. No. 60/251,147, is also incorporated by reference herein in its entirety in the manner described above for publications and references.

What is claimed is:

1. A method for treating a subject diagnosed with or at risk of developing an immunoinflammatory disorder characterized by inflammation, said method comprising administering to the subject a purified YCI polypeptide in an amount and for a time sufficient to treat said subject, wherein said purified YCI polypeptide comprises an amino acid sequence having at least 85% sequence identity to amino acids 20-137 of SEQ ID NO: 2, and wherein said purified YCI polypeptide is capable of binding to IL-18.

2. The method of claim 1, wherein said purified polypeptide comprises amino acids 20 to 137 of SEQ ID NO: 2.

3. The method of claim 1, wherein said polypeptide comprises the sequence set forth in SEQ ID NO: 2.

4. The method of claim 1, wherein said purified polypeptide sequesters said IL-18.

5. The method of claim 1, wherein said purified polypeptide inhibits the activity of said IL-18.

6. The method of claim 1, wherein said immunoinflammatory disorder is selected from the group consisting of acute inflammation, restenosis, by-pass graft occlusion, Gaucher's disease, inflammatory bowel disease, uveitis, allergic rhinitis, atopic dermatitis, food allergies, type 1 insulin-dependent diabetes mellitus, dermatitis, meningitis, Sjögren's syndrome, encephalitis, rheumatic fever, Reiter's syndrome, psoriatic arthritis, osteoarthritis, ocular inflammatory disorders, progressive systemic sclerosis, primary biliary cirrhosis, necrotizing vasculitis, polymyositis, sarcoidosis, granulomatosis, vasculitis, CNS inflammatory disorder, Hashimoto's thyroiditis, habitual spontaneous abortions, dermatomyositis, chronic active hepatitis, celiac disease, atrophic gastritis, ankylosing spondylitis, Behcet's syndrome, acute respiratory distress syndrome (ARDS), ischemic heart disease, septic shock, and cancer.

7. A pharmaceutical composition comprising a purified YCI polypeptide formulated in a pharmaceutically acceptable carrier in an amount sufficient to treat an immunoinflammatory disorder characterized by inflammation when administered to a subject, wherein said purified YCI polypeptide comprises an amino acid sequence having at least 85% sequence identity to amino acids 20-137 of SEQ ID NO: 2, and wherein said purified YCI polypeptide is capable of binding to IL-18.

8. The composition of claim 7, wherein said purified polypeptide comprises the sequence set forth in SEQ ID NO: 2.

9. A kit comprising a purified YCI polypeptide, and instructions for administering said purified polypeptide to a subject diagnosed with or at risk of developing an immunoinflammatory disorder characterized by inflammation, wherein said purified YCI polypeptide comprises an amino acid sequence having at least 85% sequence identity to amino acids 20-137 of SEQ ID NO: 2, and wherein said purified YCI polypeptide is capable of binding to IL-18.

10. A method of modulating cytokine function in a cell, said method comprising contacting said cell with a purified YCI polypeptide in an amount and for a time sufficient to modulate said cytokine function in said cell, wherein said purified YCI polypeptide comprises an amino acid sequence having at least 85% sequence identity to amino acids 20-137 of SEQ ID NO: 2, and wherein said purified YCI polypeptide is capable of binding to IL-18.

11. The method of claim 10, wherein said purified polypeptide comprises the sequence set forth in SEQ ID NO: 2.

12. The method of claim 6, wherein said immunoinflammatory disorder is selected from the group consisting of acute inflammation, restenosis, by-pass graft occlusion, Gaucher's disease, inflammatory bowel disease, uveitis, allergic rhinitis, atopic dermatitis, type 1 insulin-dependent diabetes mellitus, dermatitis, meningitis, Sjögren's syndrome, encephalitis, Reiter's syndrome, psoriatic arthritis, osteoarthritis, ocular inflammatory disorders, progressive systemic sclerosis, primary biliary cirrhosis, necrotizing vasculitis, polymyositis, sarcoidosis, granulomatosis, vasculitis, Hashimoto's thyroiditis, dermatomyositis, atrophic gastritis, ankylosing spondylitis, Behcet's syndrome, acute respiratory distress syndrome (ARDS), isohemic heart disease, septic shock, and cancer.

13. The method of claim 12, wherein said immunoinflammatory disorder is selected from the group consisting of allergic rhinitis, ankylosing spondylitis, inflammatory bowel disease, restenosis, and uveitis.

14. The method of claim 13, wherein said immunoinflammatory disorder is allergic rhinitis.

15. The method of claim 13, wherein said immunoinflammatory disorder is inflammatory bowel disease.

16. The method of claim 1, wherein the amino acid sequence of said polypeptide consists of an amino acid sequence having at least 85% sequence identity to amino acids 20 to 137 of SEQ ID NO: 2.

17. The method of claim 16, wherein the amino acid sequence of said polypeptide consists of amino acids 20 to 137 of SEQ ID NO: 2.

18. The method of claim 6, wherein the amino acid sequence of said polypeptide consists of amino acids 20 to 137 of SEQ ID NO: 2.

19. The composition of claim 7, wherein the amino acid sequence of said polypeptide consists of an amino acid sequence having at least 85% sequence identity to amino acids 20 to 137 of SEQ ID NO: 2.

20. The composition of claim 19, wherein the amino acid sequence of said polypeptide consists of amino acids 20 to 137 of SEQ ID NO: 2.

21. The kit of claim 9, wherein the amino acid sequence of said polypeptide consists of an amino acid sequence having at least 85% sequence identity to amino acids 20 to 137 of SEQ ID NO: 2.

22. The kit of claim 21, wherein the amino acid sequence of said polypeptide consists of amino acids 20 to 137 of SEQ ID NO: 2.

23. The method of claim 10, wherein the amino acid sequence of said polypeptide consists of an amino acid sequence having at least 85% sequence identity to amino acids 20 to 137 of SEQ ID NO: 2.

24. The method of claim 23, wherein the amino acid sequence of said polypeptide consists of amino acids 20 to 137 of SEQ ID NO: 2.

25. The method of claim 12, wherein the amino acid sequence of said polypeptide consists of amino acids 20 to 137 of SEQ ID NO: 2.

26. The method of claim 13, wherein the amino acid sequence of said polypeptide consists of amino acids 20 to 137 of SEQ ID NO: 2.

27. The method of claim 14, wherein the amino acid sequence of said polypeptide consists of amino acids 20 to 137 of SEQ ID NO: 2.

28. The method of claim 15, wherein the amino acid sequence of said polypeptide consists of amino acids 20 to 137 of SEQ ID NO: 2.

29. A method for treating a subject diagnosed with or at risk of developing a disorder selected from the group consisting of allergic inflammation, asthma, psoriasis, diabetes mellitus, rheumatoid arthritis, multiple sclerosis, lupus erythematosus, transplant rejection, graft rejection, glomerulonephritis, arterial restenosis, coronary occlusion, transplant vasculopathy, atherosclerosis, unstable atherosclerotic plaque rupture, and ischemic reperfusion injury, said method comprising administering to the subject a purified YCI polypeptide in an amount and for a time sufficient to treat said subject, wherein said purified YCI polypeptide comprises an amino acid sequence having at least 85% sequence identity to amino acids 20-137 of SEQ ID NO: 2, and wherein said purified YCI polypeptide is capable of binding to IL-18.

30. The method of claim 29, wherein the amino acid sequence of said polypeptide consists of an amino acid sequence having at least 85% sequence identity to amino acids 20 to 137 of SEQ ID NO: 2.

31. The method of claim 30, wherein the amino acid sequence of said polypeptide consists of amino acids 20 to 137 of SEQ ID NO: 2.

32. The method of claim 29, wherein said disorder is rheumatoid arthritis.

33. The method of claim 32, wherein the amino acid sequence of said polypeptide consists of amino acids 20 to 137 of SEQ ID NO: 2.

34. The method of claim 29, wherein said disorder is psoriasis.

35. The method of claim 34, wherein the amino acid sequence of said polypeptide consists of amino acids 20 to 137 of SEQ ID NO: 2.

36. The method of claim 29, wherein said disorder is multiple sclerosis.

37. The method of claim 36, wherein the amino acid sequence of said polypeptide consists of amino acids 20 to 137 of SEQ ID NO: 2.

38. The method of claim 29, wherein said disorder is transplant rejection.

39. The method of claim 38, wherein the amino acid sequence of said polypeptide consists of amino acids 20 to 137 of SEQ ID NO: 2.

40. The method of claim 29, wherein said polypeptide comprises amino acids 20 to 137 of SEQ ID NO: 2.

41. The composition of claim 7, wherein said polypeptide comprises amino acids 20 to 137 of SEQ ID NO: 2.

42. The kit of claim 9, wherein said polypeptide comprises amino acids 20 to 137 of SEQ ID NO: 2.

43. The method of claim 10, wherein said polypeptide comprises amino acids 20 to 137 of SEQ ID NO: 2.

44. The method of claim 1, wherein said polypeptide comprises an amino acid sequence having at least 95% sequence identity to amino acids 20-137 of SEQ ID NO: 2.

45. The method of claim 44, wherein said polypeptide comprises an amino acid sequence having at least 99% sequence identity to amino acids 20-137 of SEQ ID NO: 2.

46. The composition of claim 7, wherein said polypeptide comprises an amino acid sequence having at least 95% sequence identity to amino acids 20-137 of SEQ ID NO: 2.

47. The composition of claim 46, wherein said polypeptide comprises an amino acid sequence having at least 99% sequence identity to amino acids 20-137 of SEQ ID NO: 2.

48. The kit of claim 9, wherein said polypeptide comprises an amino acid sequence having at least 95% sequence identity to amino acids 20-137 of SEQ ID NO: 2.

49. The kit of claim 48, wherein said polypeptide comprises an amino acid sequence having at least 99% sequence identity to amino acids 20-137 of SEQ ID NO: 2.

50. The method of claim 1, wherein said purified polypeptide sequesters said IL-18.

51. The method of claim 1, wherein said purified polypeptide inhibits the activity of said IL-18.

52. The method of claim 29, wherein said polypeptide comprises an amino acid sequence having at least 95% sequence identity to amino acids 20-137 of SEQ ID NO: 2.

53. The method of claim 52, wherein said polypeptide comprises an amino acid sequence having at least 99% sequence identity to amino acids 20-137 of SEQ ID NO: 2.

* * * * *

```
                         SEQUENCE LISTING

<160> NUMBER OF SEQ ID NOS: 2

<210> SEQ ID NO 1
<211> LENGTH: 411
<212> TYPE: DNA
<213> ORGANISM: Yaba Monkey Tumor Virus

<400> SEQUENCE: 1
atgaaaaaaa ttgcaattat tttgtttttg ttgagttttt gtttttcatg tgacggtgaa      60
aaagaatgcg ataagcatag aagcgttaat attcaagttc cgatgaaaga aactagcgag     120
gtgttgttaa ggtgtaccgg tagttcgtat tttaagcatt ttagttatgt ttactggctt     180
gtgggagaaa gcgaaaccgt agatcagttg caacaaaatt ccggatatgg tgaaaccagt     240 caccccttcaa aacctcacga gtgtggaaac ttacctagcg ccgatttagt tctgacgaat    300
atgacagaaa aaatgcgtga cacaaagttg acttgtgtgt taatggaccc agacggacac     360
attgacgaat ctttagtatt acgcgaagtg tgggattgtt ttaacaaaac a              411

<210> SEQ ID NO 2
<211> LENGTH: 137
<212> TYPE: PRT
<213> ORGANISM: Yaba Monkey Tumor Virus

<400> SEQUENCE: 2

Met Lys Lys Ile Ala Ile Ile Leu Phe Leu Leu Ser Phe Cys Phe Ser
 1               5                  10                  15

Cys Asp Gly Glu Lys Glu Cys Asp Lys His Arg Ser Val Asn Ile Gln
            20                  25                  30

Val Pro Met Lys Glu Thr Ser Glu Val Leu Leu Arg Cys Thr Gly Ser
        35                  40                  45

Ser Tyr Phe Lys His Phe Ser Tyr Val Tyr Trp Leu Val Gly Glu Ser
    50                  55                  60
```

```
                                            -continued

Glu Thr Val Asp Gln Leu Gln Gln Asn Ser Gly Tyr Gly Glu Thr Ser
 65              70                  75                  80

His Pro Ser Lys Pro His Glu Cys Gly Asn Leu Pro Ser Ala Asp Leu
             85                  90                  95

Val Leu Thr Asn Met Thr Glu Lys Met Arg Asp Thr Lys Leu Thr Cys
            100                 105                 110

Val Leu Met Asp Pro Asp Gly His Ile Asp Glu Ser Leu Val Leu Arg
        115                 120                 125

Glu Val Trp Asp Cys Phe Asn Lys Thr
    130                 135
```